US011662325B2

(12) United States Patent
Sherwood et al.

(10) Patent No.: US 11,662,325 B2
(45) Date of Patent: May 30, 2023

(54) SYSTEMS AND METHODS FOR MEASURING KINETIC RESPONSE OF CHEMICAL SENSOR ELEMENTS

(71) Applicants: Boston Scientific Scimed, Inc., Maple Grove, MN (US); REGENTS OF THE UNIVERSITY OF MINNESOTA, Minneapolis, MN (US)

(72) Inventors: Gregory J. Sherwood, North Oaks, MN (US); Justin Theodore Nelson, Minneapolis, MN (US); Steven J. Koester, Edina, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 617 days.

(21) Appl. No.: 16/712,255

(22) Filed: Dec. 12, 2019

(65) Prior Publication Data
US 2020/0191737 A1 Jun. 18, 2020

Related U.S. Application Data

(60) Provisional application No. 62/781,254, filed on Dec. 18, 2018.

(51) Int. Cl.
*G01N 27/02* (2006.01)
*G01N 27/22* (2006.01)
*G01N 33/00* (2006.01)

(52) U.S. Cl.
CPC ......... *G01N 27/021* (2013.01); *G01N 27/221* (2013.01); *G01N 27/227* (2013.01); *G01N 33/0036* (2013.01)

(58) Field of Classification Search
CPC .. G01N 27/021; G01N 27/221; G01N 27/227; G01N 33/0036; G01N 27/4146; G01N 33/497
See application file for complete search history.

(56) References Cited

U.S. PATENT DOCUMENTS

| 3,661,528 A | 5/1972 | Falk |
| 3,952,730 A | 4/1976 | Key |

(Continued)

FOREIGN PATENT DOCUMENTS

| CN | 102183557 | 9/2011 |
| CN | 102941042 | 2/2013 |

(Continued)

OTHER PUBLICATIONS

"Communication Pursuant to Article 94(3) EPC," for European Patent Application No. 17733246.7 dated Jan. 28, 2022 (6 pages).

(Continued)

*Primary Examiner* — Feba Pothen
(74) *Attorney, Agent, or Firm* — Pauly, DeVries Smith & Deffner LLC

(57) ABSTRACT

Embodiments herein include a kinetic response system for measuring analyte presence on a chemical sensor element. The chemical sensor element includes one or more discrete binding detectors, each discrete binding detector including a graphene varactor. The kinetic response system includes a measurement circuit having an excitation voltage generator for generating a series of excitation cycles over a time period. Each excitation cycle includes delivering a DC bias voltage to the discrete binding detectors at multiple discrete DC bias voltages across a range of DC bias voltages. The kinetic response system includes a capacitance sensor to measure capacitance of the discrete binding detectors resulting from the excitation cycles. The kinetic response system includes a controller circuit to determine the kinetics of change in at least one of a measured capacitance value and a calculated value based on the measured capacitance over the time period. Other embodiments are also included herein.

20 Claims, 9 Drawing Sheets

(56) References Cited

U.S. PATENT DOCUMENTS

| | | |
|---|---|---|
| 3,981,297 A | 9/1976 | Dunn et al. |
| 4,820,011 A | 4/1989 | Umegaki et al. |
| 4,901,727 A | 2/1990 | Goodwin |
| 5,174,290 A | 12/1992 | Fiddian-Green |
| 5,186,172 A | 2/1993 | Fiddian-Green |
| 5,357,971 A | 10/1994 | Sheehan et al. |
| 5,423,320 A | 6/1995 | Salzman et al. |
| 5,704,368 A | 1/1998 | Asano et al. |
| 5,834,626 A | 11/1998 | De Castro et al. |
| 5,928,155 A | 7/1999 | Eggers et al. |
| 6,006,121 A | 12/1999 | Vantrappen et al. |
| 6,029,076 A | 2/2000 | Fiddian-Greene et al. |
| 6,085,576 A | 7/2000 | Sunshine et al. |
| 6,149,624 A | 11/2000 | McShane |
| 6,170,318 B1 | 1/2001 | Lewis |
| 6,192,168 B1 | 2/2001 | Feldstein et al. |
| 6,238,339 B1 | 5/2001 | Fiddian-Greene et al. |
| 6,248,078 B1 | 6/2001 | Risby et al. |
| 6,312,390 B1 | 11/2001 | Phillips et al. |
| 6,480,734 B1 | 11/2002 | Zhang et al. |
| 6,599,253 B1 | 7/2003 | Baum et al. |
| 6,615,066 B2 | 9/2003 | Huyberechts et al. |
| 6,712,770 B2 | 3/2004 | Lin et al. |
| 6,726,637 B2 | 4/2004 | Phillips et al. |
| 6,733,464 B2 | 5/2004 | Olbrich et al. |
| 6,781,690 B2 | 8/2004 | Armstrong et al. |
| 6,955,652 B1 | 10/2005 | Baum et al. |
| 6,978,182 B2 | 12/2005 | Mazar et al. |
| 7,032,431 B2 | 4/2006 | Baum et al. |
| 7,123,359 B2 | 10/2006 | Armstrong et al. |
| 7,177,686 B1 | 2/2007 | Turcott et al. |
| 7,426,848 B1 | 9/2008 | Li et al. |
| 7,459,312 B2 | 12/2008 | Chen et al. |
| 7,704,214 B2 | 4/2010 | Meixner et al. |
| 7,809,441 B2 | 10/2010 | Kane et al. |
| 7,871,572 B2 | 1/2011 | Yang et al. |
| 7,955,562 B2 | 6/2011 | Hong et al. |
| 7,972,277 B2 | 7/2011 | Oki et al. |
| 7,988,917 B2 | 8/2011 | Roesicke et al. |
| 7,992,422 B2 | 8/2011 | Leddy et al. |
| 8,043,860 B2 | 10/2011 | Leznoff et al. |
| 8,052,933 B2 | 11/2011 | Schirmer et al. |
| 8,080,206 B2 | 12/2011 | Leddy et al. |
| 8,124,419 B2 | 2/2012 | Grigorian et al. |
| 8,153,439 B2 | 4/2012 | Zamborini et al. |
| 8,154,093 B2 | 4/2012 | Passmore et al. |
| 8,157,730 B2 | 4/2012 | Tucker et al. |
| 8,222,041 B2 | 7/2012 | Pearton et al. |
| 8,244,355 B2 | 8/2012 | Bennett et al. |
| 8,294,135 B2 | 10/2012 | Lebedev et al. |
| 8,366,630 B2 | 2/2013 | Haick et al. |
| 8,479,731 B2 | 7/2013 | Heinonen et al. |
| 8,481,324 B2 | 7/2013 | Nakhoul et al. |
| 8,494,606 B2 | 7/2013 | Debreczeny et al. |
| 8,529,459 B2 | 9/2013 | Stahl, Jr. et al. |
| 8,581,262 B2 | 11/2013 | Pan et al. |
| 8,597,953 B2 | 12/2013 | Haick et al. |
| 8,747,325 B2 | 6/2014 | Bacal et al. |
| 8,828,713 B2 | 9/2014 | Ren et al. |
| 8,835,984 B2 | 9/2014 | Ren et al. |
| 8,848,189 B2 | 9/2014 | Goldshtein et al. |
| 8,951,473 B2 | 2/2015 | Wang et al. |
| 8,955,367 B2 | 2/2015 | Gouma et al. |
| 8,961,830 B2 | 2/2015 | Reynolds et al. |
| 9,011,779 B1 | 4/2015 | Anglin, Jr. et al. |
| 9,029,168 B2 | 5/2015 | Mannoor et al. |
| 9,034,170 B2 | 5/2015 | Blackburn et al. |
| 9,085,715 B2 | 7/2015 | Berthelot et al. |
| 9,103,775 B2 | 8/2015 | Bradley et al. |
| 9,138,169 B2 | 9/2015 | Beard |
| 9,147,398 B2 | 9/2015 | White et al. |
| 9,147,851 B1 | 9/2015 | Bartsch et al. |
| 9,267,908 B2 | 2/2016 | Wang et al. |
| 9,299,238 B1 | 3/2016 | Ahmad et al. |
| 9,315,848 B2 | 4/2016 | Haick et al. |
| 9,316,637 B2 | 4/2016 | Ren et al. |
| 9,324,825 B2 | 4/2016 | Ravesi et al. |
| 9,366,664 B2 | 6/2016 | Anglin, Jr. et al. |
| 9,410,040 B2 | 8/2016 | Li et al. |
| 9,513,244 B2 | 12/2016 | Koester |
| 9,528,979 B2 | 12/2016 | Haick et al. |
| 9,618,476 B2 | 4/2017 | Goldsmith |
| 9,638,169 B2 | 5/2017 | Obrecht |
| 9,642,577 B1 | 5/2017 | Li et al. |
| 9,671,392 B2 | 6/2017 | Jeppsen et al. |
| 9,689,836 B2 | 6/2017 | Makaram et al. |
| 9,696,311 B2 | 7/2017 | Haick et al. |
| 9,763,600 B2 | 9/2017 | Van Kesteren et al. |
| 9,765,395 B2 | 9/2017 | Goldsmith |
| 9,775,241 B2 | 9/2017 | Walczak et al. |
| 9,859,034 B2 | 1/2018 | Sjong |
| 9,936,897 B2 | 4/2018 | Carlson et al. |
| 9,977,011 B2 | 5/2018 | Beck et al. |
| 10,034,621 B2 | 7/2018 | Wondka et al. |
| 10,046,323 B2 | 8/2018 | Bos |
| 10,307,080 B2 | 6/2019 | Ssenyange et al. |
| 10,493,276 B2 | 12/2019 | Moffitt et al. |
| 10,543,035 B2 | 1/2020 | Sutermeister et al. |
| 10,770,182 B2 | 9/2020 | Sherwood et al. |
| 10,852,264 B2 | 12/2020 | Kelly et al. |
| 11,079,371 B2 | 8/2021 | Zhen et al. |
| 11,085,921 B2 | 8/2021 | Livache et al. |
| 11,172,846 B2 | 11/2021 | Sherwood et al. |
| 11,191,457 B2 | 12/2021 | Sherwood et al. |
| 11,262,354 B2 | 3/2022 | Sherwood |
| 2002/0123749 A1 | 9/2002 | Jain et al. |
| 2002/0142477 A1 | 10/2002 | Lewis et al. |
| 2003/0051733 A1 | 3/2003 | Kotmel et al. |
| 2004/0039295 A1 | 2/2004 | Olbrich et al. |
| 2006/0130557 A1 | 6/2006 | Leddy et al. |
| 2006/0263255 A1 | 11/2006 | Han et al. |
| 2006/0270940 A1 | 11/2006 | Tsukashima et al. |
| 2007/0048181 A1 | 3/2007 | Chang et al. |
| 2007/0083094 A1 | 4/2007 | Colburn et al. |
| 2007/0167853 A1 | 7/2007 | Melker et al. |
| 2007/0229818 A1 | 10/2007 | Duan et al. |
| 2007/0265509 A1 | 11/2007 | Burch et al. |
| 2008/0021339 A1 | 1/2008 | Gabriel et al. |
| 2008/0038154 A1 | 2/2008 | Longbottom et al. |
| 2008/0052122 A1 | 2/2008 | Iliff |
| 2008/0146890 A1 | 6/2008 | Leboeuf et al. |
| 2008/0161709 A1 | 7/2008 | Bradley |
| 2008/0183910 A1 | 7/2008 | Natoli et al. |
| 2008/0228098 A1 | 9/2008 | Popov et al. |
| 2008/0317636 A1 | 12/2008 | Brahim et al. |
| 2009/0054799 A1 | 2/2009 | Vrtis et al. |
| 2009/0104435 A1 | 4/2009 | Hutchison et al. |
| 2009/0112115 A1 | 4/2009 | Huang et al. |
| 2009/0230300 A1 | 9/2009 | Trevejo et al. |
| 2010/0024533 A1 | 2/2010 | Kimura et al. |
| 2010/0056892 A1 | 3/2010 | Ben-Barak et al. |
| 2010/0085067 A1 | 4/2010 | Gabriel et al. |
| 2010/0137733 A1 | 6/2010 | Wang et al. |
| 2010/0147303 A1 | 6/2010 | Jafari et al. |
| 2010/0188069 A1 | 7/2010 | Ren et al. |
| 2010/0198521 A1 | 8/2010 | Haick et al. |
| 2010/0216175 A1 | 8/2010 | Melker et al. |
| 2010/0268479 A1* | 10/2010 | Potyrailo ............ G01N 27/026 702/23 |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0059476 A1 | 3/2011 | Shin et al. |
| 2011/0143962 A1 | 6/2011 | Chaubron et al. |
| 2011/0201956 A1 | 8/2011 | Alferness et al. |
| 2011/0269632 A1 | 11/2011 | Haick et al. |
| 2011/0283770 A1 | 11/2011 | Hok et al. |
| 2012/0100636 A1* | 4/2012 | Johal .................... G01N 33/557 422/69 |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | Leboeuf et al. |

(56) References Cited

U.S. PATENT DOCUMENTS

| | | |
|---|---|---|
| 2012/0226111 A1 | 9/2012 | Leboeuf et al. |
| 2012/0226112 A1 | 9/2012 | Leboeuf et al. |
| 2012/0245434 A1 | 9/2012 | Haick et al. |
| 2012/0245854 A1 | 9/2012 | Haick et al. |
| 2012/0277794 A1 | 11/2012 | Kountotsis et al. |
| 2012/0306802 A1 | 12/2012 | McCracken |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0100067 A1 | 4/2013 | Dews |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0165810 A1 | 6/2013 | Saatchi et al. |
| 2013/0171733 A1 | 7/2013 | Haick et al. |
| 2013/0178756 A1 | 7/2013 | Suzuki et al. |
| 2013/0211207 A1 | 8/2013 | Joseph et al. |
| 2013/0211852 A1 | 8/2013 | Roizen et al. |
| 2013/0224761 A1 | 8/2013 | Imberty et al. |
| 2013/0236981 A1 | 9/2013 | Haick et al. |
| 2013/0253358 A1 | 9/2013 | Phillips et al. |
| 2013/0267862 A1 | 10/2013 | Jaffe et al. |
| 2013/0289368 A1 | 10/2013 | Covington et al. |
| 2013/0331723 A1 | 12/2013 | Hernandez-Silveira et al. |
| 2013/0334579 A1 | 12/2013 | Accardi et al. |
| 2014/0018691 A1 | 1/2014 | Mcneill et al. |
| 2014/0041436 A1 | 2/2014 | Knott et al. |
| 2014/0051956 A1 | 2/2014 | Dalene et al. |
| 2014/0094669 A1 | 4/2014 | Jaffe et al. |
| 2014/0122515 A1 | 5/2014 | Lee et al. |
| 2014/0145735 A1 | 5/2014 | Koester et al. |
| 2014/0171817 A1 | 6/2014 | Blanch et al. |
| 2014/0194703 A1 | 7/2014 | Wondka et al. |
| 2014/0275597 A1 | 9/2014 | Zhang et al. |
| 2014/0276168 A1 | 9/2014 | Satya et al. |
| 2014/0294675 A1 | 10/2014 | Melker et al. |
| 2014/0318535 A1 | 10/2014 | Bullock et al. |
| 2014/0378790 A1 | 12/2014 | Cohen |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Ahmad |
| 2015/0164373 A1 | 6/2015 | Davis et al. |
| 2015/0196251 A1 | 7/2015 | Outwater et al. |
| 2015/0250408 A1 | 9/2015 | Ssenyange et al. |
| 2015/0257676 A1 | 9/2015 | Fries |
| 2015/0265184 A1 | 9/2015 | Wondka et al. |
| 2015/0295562 A1 | 10/2015 | Agarwal et al. |
| 2015/0298115 A1 | 10/2015 | Campidelli et al. |
| 2015/0301021 A1 | 10/2015 | Haick et al. |
| 2015/0307936 A1 | 10/2015 | Goldsmith |
| 2015/0309018 A1 | 10/2015 | Goldsmith |
| 2015/0320338 A1 | 11/2015 | Kane et al. |
| 2015/0335266 A1 | 11/2015 | Cormier |
| 2015/0335267 A1 | 11/2015 | Cormier et al. |
| 2015/0338340 A1 | 11/2015 | Jiang et al. |
| 2015/0338390 A1 | 11/2015 | Anglin et al. |
| 2015/0351699 A1 | 12/2015 | Addison et al. |
| 2016/0025675 A1 | 1/2016 | Goldsmith |
| 2016/0054312 A1 | 2/2016 | Goldsmith |
| 2016/0089089 A1 | 3/2016 | Kakkar et al. |
| 2016/0093806 A1 | 3/2016 | Turchanin |
| 2016/0109440 A1 | 4/2016 | Sherwood et al. |
| 2016/0116431 A1 | 4/2016 | Accardi et al. |
| 2016/0150995 A1 | 6/2016 | Ratto et al. |
| 2016/0157752 A1 | 6/2016 | Cho et al. |
| 2016/0192861 A1 | 7/2016 | Gedeon et al. |
| 2016/0231309 A1 | 8/2016 | Ahmad et al. |
| 2016/0289769 A1 | 10/2016 | Schwartz et al. |
| 2016/0334381 A1 | 11/2016 | King-smith et al. |
| 2016/0334386 A1 | 11/2016 | Anglin et al. |
| 2016/0356741 A1 | 12/2016 | Makaram et al. |
| 2016/0370337 A1 | 12/2016 | Blackley |
| 2017/0014043 A1 | 1/2017 | McDonnell |
| 2017/0042435 A1 | 2/2017 | Vermeulen et al. |
| 2017/0053068 A1 | 2/2017 | Pillai et al. |
| 2017/0067888 A1 | 3/2017 | Taslim et al. |
| 2017/0082566 A1 | 3/2017 | Koester |
| 2017/0212116 A1 | 7/2017 | Braga et al. |
| 2017/0227491 A1 | 8/2017 | Johnson et al. |
| 2017/0307562 A1 | 10/2017 | Goldsmith |
| 2017/0307576 A1 | 10/2017 | Anglin, Jr. et al. |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2018/0037985 A1 | 2/2018 | Myers et al. |
| 2018/0110444 A1 | 4/2018 | Sherwood et al. |
| 2018/0328841 A1 | 11/2018 | Graham et al. |
| 2018/0336970 A1 | 11/2018 | Sherwood et al. |
| 2019/0025237 A1 | 1/2019 | Kelly et al. |
| 2019/0178837 A1 | 6/2019 | Xu et al. |
| 2019/0254538 A1 | 8/2019 | Erdman et al. |
| 2019/0257825 A1 | 8/2019 | Zhen et al. |
| 2019/0286866 A1 | 9/2019 | Gurt |
| 2019/0331661 A1 | 10/2019 | Zhen et al. |
| 2020/0166435 A1 | 5/2020 | Sherwood et al. |
| 2021/0057526 A1 | 2/2021 | Zhen et al. |
| 2021/0072208 A1 | 3/2021 | Sherwood et al. |
| 2021/0148848 A1 | 5/2021 | Kelly et al. |
| 2021/0341409 A1 | 11/2021 | Rognrud et al. |
| 2022/0334075 A1 | 10/2022 | Koester et al. |

FOREIGN PATENT DOCUMENTS

| | | |
|---|---|---|
| CN | 103332678 | 10/2013 |
| CN | 103950920 | 7/2014 |
| CN | 104914138 | 9/2015 |
| CN | 103852505 | 11/2015 |
| CN | 103877574 | 1/2016 |
| CN | 105445335 | 3/2016 |
| CN | 105527321 | 4/2016 |
| CN | 105688995 | 6/2016 |
| CN | 106152924 | 11/2016 |
| CN | 107180706 | 9/2017 |
| EP | 1764153 | 3/2007 |
| EP | 1806414 | 7/2007 |
| EP | 3093653 | 11/2016 |
| EP | 3431977 | 1/2019 |
| IN | 201627028955 | 10/2016 |
| JP | H11174051 | 7/1999 |
| JP | 2009244074 | 10/2009 |
| JP | 2011102747 | 5/2011 |
| JP | 2012122814 | 6/2012 |
| JP | 2016022415 | 2/2016 |
| JP | 2016122249 | 7/2016 |
| JP | 2017123912 | 7/2017 |
| KR | 20170057001 | 5/2017 |
| KR | 101797737 | 11/2017 |
| WO | 9325142 | 12/1993 |
| WO | 9947905 | 9/1999 |
| WO | 2001070114 | 9/2001 |
| WO | 2008088780 | 7/2008 |
| WO | 2009135070 | 11/2009 |
| WO | 2011109736 | 9/2011 |
| WO | 2012135565 | 10/2012 |
| WO | 2012145247 | 10/2012 |
| WO | 2013095730 | 6/2013 |
| WO | 2013189502 | 12/2013 |
| WO | 2014064740 | 5/2014 |
| WO | 2015179623 | 11/2015 |
| WO | 2015191558 | 12/2015 |
| WO | 2016064740 | 4/2016 |
| WO | 2016105464 | 6/2016 |
| WO | 2016145300 | 9/2016 |
| WO | 2017066583 | 4/2017 |
| WO | 2017095922 | 6/2017 |
| WO | 2017218464 | 12/2017 |
| WO | 2018075731 | 4/2018 |

(56) References Cited

FOREIGN PATENT DOCUMENTS

| WO | 2018213564 | 11/2018 |
|---|---|---|
| WO | 2020102880 | 5/2020 |
| WO | 2020112825 | 6/2020 |

OTHER PUBLICATIONS

"Communication Pursuant to Article 94(3) EPC," for European Patent Application No. 17794832.0 dated Mar. 7, 2022 (9 pages).
"First Office Action," for Chinese Patent Application No. 201810782878.3 dated Feb. 9, 2022 (14 pages) with English Summary.
"Office Action," for Japanese Patent Application No. 2018-133996 dated Jan. 25, 2022 (7 pages) with English Translation.
Notice of Allowance for U.S. Appl. No. 16/037,218 dated Jul. 31, 2020 (20 pages).
Response to Communication Pursuant to Rules 161(1) and 162 EPC for European Patent Application No. 18731579.1 filed Jul. 17, 2020 (19 pages).
Response to Final Rejection dated Jun. 8, 2020 and Advisory Action dated Sep. 4, 2020, for U.S. Appl. No. 15/621,103, submitted via EFS-Web on Oct. 8, 2020, 16 pages.
Response to Final Rejection dated Jun. 8, 2020 for U.S. Appl. No. 15/621,103, submitted via EFS-Web on Aug. 20, 2020, 16 pages.
Response to Non-Final Rejection dated Jun. 29, 2020 for U.S. Appl. No. 15/787,985, submitted via EFS-Web on Sep. 29, 2020, 9 pages.
Non-Final Office Action for U.S. Appl. No. 15/787,985 dated Jun. 29, 2020 (14 pages).
Office Action for Japanese Patent Application No. 2019-520955 dated Jul. 14, 2020 (5 pages) No English Translation.
Response to Final Rejection dated May 1, 2020 for U.S. Appl. No. 14/883,895, submitted via EFS-Web on Jul. 15, 2020, 12 pages.
Response to Non-Final Rejection dated Apr. 29, 2020 for U.S. Appl. No. 16/037,218, submitted via EFS-Web on Jul. 15, 2020, 7 pages.
Final Office Action for U.S. Appl. No. 15/621,103 dated Jun. 8, 2020 (21 pages).
Response to Non-Final Rejection dated Feb. 21, 2020 for U.S. Appl. No. 15/621,103, submitted via EFS-Web on May 20, 2020.
Arasaradnam, R. P. et al., "Review Article: Next Generation Diagnostic Modalities in Gastroenterology—Gas Phase Volatile compound biomarker detection," Alimentary Pharmacology and Therapeutics 2014; 39: 780-789 (10 pages).
Bhadra, Sharmista et al., "Non-destructive detection offish spoilage using a wireless basic volatile sensor," Talanta, vol. 134, Dec. 25, 2014 pp. 718-723 (6 pages).
Boots, Agnes W. et al., "The Versatile Use of Exhaled Volatile Organic Compounds in Human Health and Disease," J. Breath Res. 6 (2012) 027108 (21 pages).
Chamberlain II, Richard V. et al., "Electrostatically-induced Inclusion of Anions in Cyclodextrin Monolayers on Electrodes," Langmuir 2000, 1388-1396 (9 pages).
"Communication Pursuant to Article 94(3) EPC," for European Patent Application No. 15790739.5 dated Dec. 17, 2019 (5 pages).
"Communication Pursuant to Article 94(3) EPC," for European Patent Application No. 18180455.0 dated Dec. 20, 2019 (3 pages).
"Communication Pursuant to Article 94(3) EPC," for European Patent Application No. 18180455.0 dated Feb. 11, 2019 (6 pages).
"Communication Pursuant to Article 94(3) EPC," for European Patent Application No. 18180455.0 dated Jul. 15, 2019 (5 pages).
Deen, David A. et al., "Graphene-Based Quantum Capacitance Wireless Vapor Sensors," IEEE Sensors Journal, vol. 14, No. 5, May 2014, pp. 1459-1466 (8 pages).
Di Natale, Corrado et al., "Lung Cancer Identification by the Analysis of Breath by Means of an Array of Non-Selective Gas Sensors," Biosensors and Bioelectronics 18 (2003) 1209-1218 (10 pages).
Droscher, S. et al., "Quantum Capacitance and Density of States of Graphene," Phys. Scr. T146 (2012) 014009, pp. 1-5 (5 pages).
Ebrish, M. A. et al., "Dielectric Thickness Dependence of Quantum Capacitance in Graphene Varactors with Local Metal Back Gates," Device Research Conference, 2012 (2 pages).
Ebrish, M. A. et al., "Operation of Multi-Finger Graphene Quantum Capacitance Varactors using Planarized Local Bottom Gate Electrodes," Applied Physics Letters, vol. 100, No. 14, Apr. 2012 (4 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
"European Search Report," for Dutch Patent Application No. 2019492 dated Apr. 12, 2018 (10 pages).
"European Search Report," for European Patent Application No. 18180455.0 dated Dec. 3, 2018 (5 pages).
"FDC1004 4-Channel Capacitance-to-Digital Converter for Capacitive Sensing Solutions," Data Sheet SNOSCY5B Texas Instruments Aug. 2014—Revised 2015 (24 pages).
"FDC1004EVM User Guide," Literature No. SNAU163C, Texas Instruments August 2014—Revised Oct. 2016 (46 pages).
"File History," for U.S. Appl. No. 14/883,895 retrieved May 14, 2020 (301 pages).
"Final Office Action," for U.S. Appl. No. 15/787,985 dated Jan. 17, 2020 (16 pages).
"First Office Action," for Chinese Patent Application No. 201580056417.2 dated Feb. 11, 2019 (13 pages) with English summary.
Fisher, James P. et al., "Central Sympathetic Overactivity: Maladies and Mechanisms," Autonomic Neuroscience 148.1 (2009): 5-15 (11 pages).
Georgakilas, Vasilios et al., "Functionalization of Graphene: Covalent and Non-Covalent Approaches, Derivatives and Applications," Chemical Reviews, 2012, 14:112(11), pp. 6156-6214.
Georgakilas, Vasilios et al., "Noncovalent Functionalization of Graphene and Graphene Oxide for Energy Materials, Biosensing, Catalytic, and Biomedical Applications," Chem. Rev. 2016, 116, 5464-5519 (56 pages).
Guo, Yujing et al., "Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).
Hu, Yuhai et al., "Chemically Functionalized Graphene and Their Applications in Electrochemical Energy Conversion and Storage," Advances in Graphene Science, Chapter 7, 2013, pp. 161-190 (30 pages).
"International Preliminary Report on Patentability," for PCT Application No. PCT/US2015/056243 dated May 4, 2017 (8 pages).
"International Preliminary Report on Patentability," for PCT Application No. PCT/US2017/057318 dated May 2, 2019 (11 pages).
"International Preliminary Report on Patentability," for PCT Application No. PCT/US2018/033166 dated Nov. 28, 2019 (8 pages).
"International Preliminary Report on Patentability," for PCT Application No. PCT/US2018/03/144 dated Dec. 27, 2018 (7 pages).
"International Search Report and Written Opinion," for PCT Application No. PCT/US2015/056243, dated Jan. 26, 2016 (12 pages).
"International Search Report and Written Opinion," for PCT Application No. PCT/US2017/037144 dated Oct. 6, 2017 (11 pages).
"International Search Report and Written Opinion," for PCT Application No. PCT/US2017/057318 dated Feb. 6, 2018 (14 pages).
"International Search Report and Written Opinion," for PCT Application No. PCT/US2018/033166 dated Oct. 2, 2018 (12 pages).
"International Search Report and Written Opinion," for PCT Application No. PCT/US2019/063324 dated Mar. 27, 2020 (17 pages).
"International Search Report and Written Opinion," for PCT Application No. PCT/US2019/065981 dated Mar. 16, 2020 (14 pages).
Koester, Steven J. "High Quality Factor Graphene Varactors for Wireless Sensing Applications," Applied Physics Letters 99, 163105 (2011), 3 pages.
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Li, Xiao et al., "Digital Health: Tracking Physiomes and Activity Using Wearable Biosensors Reveals Useful Health-Related Information," PLoS Biology 15.1 (2017): e2001402 (30 pages).

(56) References Cited

OTHER PUBLICATIONS

Ma, Rui et al., "Acetone Sensing Using Graphene Quantum Capacitance Varactors," 2016 IEEE Sensors, Orlando, FL, 2016 (3 pages).

Machado, Roberto F. et al., "Detection of Lung Cancer by Sensor Array Analyses of Exhaled Breath," Am J Respir Crit Care Med, vol. 171, 1286-1291 (2005), 6 pages.

"Mechanical Data," DGS (S-PDSO-G10) DSC0010B Package Outline, Example Board Layout, and Stencil Design. Texas Instruments 2016 (5 pages).

Nakhleh, Morad K. et al., "Diagnosis and Classification of 17 Diseases from 1404 Subjects via Pattern Analysis of Exhaled Molecules," ACS Nano 2017, 11, 112-125 (14 pages).

"Nano Mobile Healthcare Inc.," Company Profile on Reuters.com URL <http://www.reuters.com/finance/stocks/companyProfile?symbol=VNTH.PK> accessed Mar. 17, 2017 (2 pages).

Navaneethan, Udayakumar et al., "Volatile Organic Compounds in Bile Can Diagnose Malignant Biliary Strictures in the Setting of Pancreatic Cancer: A Preliminary Observation," Gastrointest Endosc. Dec. 2014;80(6):1038-45 (8 pages).

"Non-Final Office Action," for U.S. Appl. No. 15/621,103 dated Feb. 21, 2020 (58 pages).

"Non-Final Office Action," for U.S. Appl. No. 15/787,985 dated Oct. 10, 2019 (40 pages).

"Non-Final Office Action," for U.S. Appl. No. 15/982,506 dated Dec. 11, 2019 (41 pages).

"Non-Final Office Action," for U.S. Appl. No. 16/037,218 dated Apr. 29, 2020 (46 pages).

"Notice of Allowance,"for U.S. Appl. No. 15/982,506 dated May 7, 2020 (17 pages).

"Office Action," for Japanese Patent Application No. 2019-517196 dated Feb. 4, 2020 (10 pages) with English Translation.

Olson, Eric J. et al., "Capacitive Sensing of Intercalated H2O Molecules Using Graphene," ACS Appl. Mater. Interfaces 2015, 7(46), 25804-25812 (29 pages).

Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).

"Package Materials Information," Tape and Reel Information and Box Dimensions. Texas Instruments Feb. 13, 2016 (2 pages).

"Package Option Addendum," Packaging Information for FDC1004DGSR, DGST, DSCJ, DSCR and DSCT Devices. Texas Instruments May 2015 (2 pages).

Putta, Chandrababu et al., "Palladium Nanoparticles on Beta-Cyclodextrin Functionalised Graphene Nanosheets: a Supramolecular Based Heterogeneous Catalyst for C—C Coupling Reactions under Green Reaction Conditions," RSC Adv., 2015, 5, 6652-6660 (9 pages).

"Response to Communication Pursuant to Article 94(3) EPC," for European Patent Application No. 15790739.5 filed Apr. 24, 2020 (16 pages).

"Response to Communication Pursuant to Article 94(3) EPC," for European Patent Application No. 18180455.0 filed Apr. 21, 2020 (24 pages).

"Response to Communication Pursuant to Article 94(3) EPC," for European Patent Application No. 18180455.0 filed Jun. 6, 2019 (44 pages).

"Response to Communication Pursuant to Article 94(3) EPC," for European Patent Application No. 18180455.0 filed Nov. 12, 2019 (9 pages).

"Response to Communication Pursuant to Rules 161(1) and 162 EPC," for European Patent Application No. 15790739.5 filed with the EPO Dec. 8, 2017 (14 pages).

"Response to Communication Pursuant to Rules 161(1) and 162 EPC," for European Patent Application No. 17733246.7 filed May 29, 2019 (22 pages).

"Response to Communication Pursuant to Rules 161(1) and 162 EPC," for European Patent Application No. 17794832.0 filed Dec. 6, 2019 (9 pages).

"Response to Final Rejection," dated Jan. 17, 2020 for U.S. Appl. No. 15/787,985, submitted via EFS-Web on Apr. 9, 2020, 12 pages.

"Response to Non-Final Rejection," dated Dec. 11, 2019 for U.S. Appl. No. 15/982,506, submitted via EFS-Web on Feb. 25, 2020, 13 pages.

"Response to Non-Final Rejection," dated Oct. 10, 2019 for U.S. Appl. No. 15/787,985, submitted via EFS-Web on Jan. 7, 2020, 17 pages.

Rojas, Maria T. et al., "Supported Monolayers Containing Preformed Binding-Sites—Synthesis and Interfacial Binding-Properties of a Thiolated Beta-Cyclodextrin Derivative," J. Am. Chem. Soc. 1995, 117, 336-343 (8 pages).

"Standard Terms and Conditions for Evaluation Modules," Texas Instruments 2016 (5 pages).

Tripathi, Kumud M. et al., "Recent Advances in Engineered Graphene and Composites for Detection of Volatile Organic Compounds (VOCs) and Non-Invasive Diseases Diagnosis," Carbon 110 (2016)97-129 (34 pages).

Wang, David "FDC1004: Basics of Capacitive Sensing and Applications," Application Report SNOA927, Texas Instruments Dec. 2014 (12 pages).

Wayu, Mulugeta B. et al., "Electropolymerization of Beta-Cyclodextrin onto Multi-Walled Carbon Nanotube Composite Films for Enhanced Selective Detection of Uric Acid," Journal of Electroanalytical Chemistry 783 (2016), 192-200 (9 pages).

Zhang, Yao et al., "Capacitive Sensing of Glucose in Electrolytes using Graphene Quantum Capacitance Varactors," ACS Appl. Mater. Interfaces 2017, 9, 38863-38869 (7 pages).

Zhang, Yao et al., "Glucose Sensing with Graphene Varactors," IEEE Sensors, Sensors 2016—Proceedings, Orlando, FL 2016 (3 pages).

Zhen, Xue et al., "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).

"International Preliminary Report on Patentability," for PCT Application No. PCT/US2019/065981 dated Jul. 1, 2021 (8 pages).

"International Search Report and Written Opinion," for PCT Application No. PCT/US2021/026778 dated Aug. 3, 2021 (11 pages).

"New Summons to Attend Oral Proceedings," for European Patent Application No. 18731579.1 dated Jul. 12, 2021 (6 pages).

"Notice of Allowance," for U.S. Appl. No. 15/621,103 dated Aug. 3, 2021 (18 pages).

"Notice of Allowance," for U.S. Appl. No. 15/787,985 dated Jul. 15, 2021 (14 pages).

"Response to Final Rejection," dated Apr. 22, 2021 and the Advisory Action dated Jul. 8, 2021 for U.S. Appl. No. 15/621,103, submitted via EFS-Web on Jul. 12, 2021, 13 pages.

"Summons to attend oral proceedings pursuant to Rule 115(1) EPC," for European Patent Application No. 18731579.1 dated Jul. 1, 2021 (6 pages).

Planz, B., et al. "The role of urinary cytology for detection of bladder cancer," EJSO (2005) 21, 304-308 (5 pages).

Ramakumar, Sanjay, et al. "Comparison of Screening Methods in the Detection of Bladder Cancer," The Journal of Urology vol. 161, 388-394, Feb. 1999 (7 pages).

"Extended European Search Report," for European Patent Application No. 20214733.6 dated Apr. 21, 2021 (11 pages).

"Final Office Action," for U.S. Appl. No. 15/621,103 dated Apr. 22, 2021 (20 pages).

"Non-Final Office Action," for U.S. Appl. No. 14/883,895 dated May 20, 2021 (34 pages).

Zhang, Xu et al., "A Wide Measurement Range and Fast Update Rate Integrated Interface for Capacitive Sensors Array," IEEE Transactions on Circuits and Systems—1: Regular Papers, Vo. 61, No. 1, Jan. 2014, pp. 2-11 (10 pages).

"International Preliminary Report on Patentability," for PCT Application No. PCT/US2019/063324 dated Jun. 10, 2021 (10 pages).

"Office Action," for Chinese Patent Application No. 201780065376.2 dated Apr. 27, 2021 (10 pages) with English Summary.

"Response to Final Rejection," dated Apr. 22, 2021 for U.S. Appl. No. 15/621,103, submitted via EFS-Web on Jun. 22, 2021, 13 pages.

"Response to Non-Final Rejection," dated Apr. 16, 2021 for U.S. Appl. No. 15/787,985, submitted via EFS-Web on Jun. 22, 2021, 11 pages.

(56) References Cited

OTHER PUBLICATIONS

"Second Office Action," for Chinese Patent Application No. 201780030595.7 dated Jun. 17, 2021 (8 pages), with English Summary.
Communication Pursuant to Article 94(3) EPC for European Patent Application No. 18731579.1 dated Nov. 10, 2020 (5 pages).
Final Office Action for U.S. Appl. No. 15/787,985 dated Oct. 21, 2020 (21 pages).
First Office Action for Chinese Patent Application No. 201780030595.7 dated Nov. 2, 2020 (12 pages) with English Summary.
Non-Final Office Action for U.S. Appl. No. 15/621,103 dated Oct. 23, 2020 (27 pages).
Office Action for Japanese Patent Application No. 2019-563876 dated Nov. 4, 2020 (3 pages) No English Translation.
"Office Action," for Japanese Patent Application No. 2019-520955 dated Feb. 9, 2021 (11 pages) with English Translation.
"Response to Communication Pursuant to Article 94(3) EPC," for European Patent Application No. 18731579.1 filed Mar. 15, 2021 (12 pages).
"Response to Final Rejection," dated Oct. 21, 2020 for U.S. Appl. No. 15/787,985, submitted via EFS-Web on Jan. 21, 2021, 8 pages.
"Response to Non-Final Rejection," dated Oct. 23, 2020 for U.S. Appl. No. 15/621,103, submitted via EFS-Web on Jan. 22, 2021, 17 pages.
"Decision of Rejection," for Chinese Patent Application No. 201780065376.2 dated Apr. 1, 2022 (9 pages) with English Translation.
"Non-Final Office Action," for U.S. Appl. No. 17/101,900 dated Mar. 31, 2022 (16 pages).
"Response to Communication Pursuant to Article 94(3) EPC," for European Patent Application No. 17733246.7 filed May 18, 2022 (9 pages).
"First Office Action," for Chinese Patent Application No. 201880032911.9 dated Nov. 3, 2021 (11 pages) with English Summary.
"Non-Final Office Action," for U.S. Appl. No. 17/101,900 dated Sep. 20, 2021 (48 pages).
"Notice of Allowance," for U.S. Appl. No. 14/883,895 dated Oct. 22, 2021 (18 pages).
"Response to Communication Pursuant to Rules 161(1) and 162 EPC," for European Patent Application No. 19828373.1 filed Nov. 8, 2021 (22 pages).
"Response to Communication Pursuant to Rules 161(1) and 162 EPC," for European Patent Application No. 19836341.8 filed Jan. 7, 2022 (12 pages).
"Response to Communication Pursuant to Rules 70(2) and 70a(2)/Rule 39(1)," for European Patent Application No. 20214733.6 filed Nov. 23, 2021 (4 pages).
"Response to Non-Final Rejection," dated Sep. 20, 2021 for U.S. Appl. No. 17/101,900, submitted via EFS-Web on Dec. 20, 2021, 10 pages.
"Second Office Action," for Chinese Patent Application No. 201780065376.2 dated Nov. 16, 2021 (8 pages) with English Summary.
"Written Submission," in Response to Summons to Attend Oral Proceedings for European Patent Application No. 18731579.1 filed Nov. 30, 2021 (31 pages).
Groves, William A., et al."Analysis of Solvent Vapors in Breath and Ambient Air with a Surface Acoustic Wave Sensor Array," Ann. Occup. Hyg., vol. 45, No. 8, pp. 609-623, 2001 (15 pages).
"Communication Pursuant to Article 94(3) EPC," for European Patent Application No. 15790739.5 dated Jun. 3, 2022 (5 pages).
"Determination of Carbonyl Compounds By High performance Liquid Chromatography (HPLC)," EPA Method 8315A 1996 (34 pages).
"First Examination Report," for Australian Patent Application No. 2019224011 dated Apr. 9, 2021 (4 pages).
"International Preliminary Report on Patentability," for PCT Application No. PCT/US2019/018741 dated Sep. 3, 2020 (11 pages).

"International Preliminary Report on Patentability," for PCT Application No. PCT/US2019/028870 dated Nov. 5, 2020 (11 pages).
"International Search Report and Written Opinion," for PCT Application No. PCT/US2019/018741 dated May 6, 2019 (17 pages).
"International Search Report and Written Opinion," for PCT Application No. PCT/US2019/028870 dated Aug. 20, 2019 (17 pages).
"International Search Report and Written Opinion," for PCT Application No. PCT/US2020/046829 dated Nov. 18, 2020 (15 pages).
"International Search Report and Written Opinion," for PCT Application No. PCT/US2022/025004 dated Jul. 25, 2022 (15 pages).
"Non-Final Office Action," for U.S. Appl. No. 16/280,635 dated Feb. 10, 2021 (40 pages).
"Non-Final Office Action," for U.S. Appl. No. 16/393,177 dated May 25, 2021 (37 pages).
"Non-Final Office Action," for U.S. Appl. No. 16/696,348 dated Jun. 20, 2022 (68 pages).
"Notice of Allowance," for U.S. Appl. No. 16/280,635 dated Mar. 31, 2021 (14 pages).
"Office Action," for Japanese Patent Application No. 2018-133996 dated Jul. 12, 2022 (4 pages) with English Translation.
"Response to Communication Pursuant to Article 94(3) EPC," for European Patent Application No. 17794832.0 filed Jul. 7, 2022 (8 pages).
"Response to Communication Pursuant to Rules 161(1) and 162 EPC," for European Patent Application No. 19709268.7 filed Apr. 1, 2021 (12 pages).
"Response to Communication Pursuant to Rules 161(1) and 162 EPC," for European Patent Application No. 19733177.0 filed Jun. 4, 2021 (20 pages).
"Response to Examination Report," for Australian Patent Application No. 2019224011 filed Jul. 23, 2021 (22 pages).
"Response to Non-Final Rejection," dated Feb. 10, 2021 for U.S. Appl. No. 16/280,635, submitted via EFS-Web on Mar. 17, 2021, 16 pages.
"Response to Non-Final Rejection," dated Mar. 31, 2022 for U.S. Appl. No. 17/101,900, submitted via EFS-Web on Jun. 28, 2022, 11 pages.
"Response to Non-Final Rejection," dated May 20, 2021 for U.S. Appl. No. 14/883,895, submitted via EFS-Web on Aug. 19, 2021, 12 pages.
Agbonlahor, Osazuwa, et al. "Adsorbed Molecules as Interchangeable Dopants and Scatterers with a van der Waals Bonding Memory in Graphene Sensors," ACS Sens. 2020, 5 (7), 2003-2009 (13 pages).
Allen, Matthew J., et al. "Honeycomb Carbon: A Review of Graphene," Chem. Rev. 2010, 110, 132-145 (14 pages).
An, Xiaohong, et al. "Stable Aqueous Dispersions of Noncovalently Functionalized Graphene from Graphite and their Multifunctional High-Performance Applications," Nano Lett. 2010, 10, 4295-4301 (7 pages).
Bair, Kenneth W., et al. "(1-Pyrenylmethyl)amino Alcohols, a New Class of Antitumor DNA intercalators. Discovery and Initial Amine Side Chain Structure-Activity Studies," J. Med. Chem. 1990, 33, 2385-2393 (9 pages).
Bard, Allen J., et al. "Electrochemical Methods: Fundamentals and Applications," Wiley New York: 1980; vol. 2 (850 pages).
Bartosik, Miroslav, et al. "The mechanism and suppression of physisorbed-water caused hysteresis in graphene FET sensors," ACS Sens., vol. 5, 2940-2949 (2020). (40 pages).
Biedermann, Frank, et al. "Experimental Binding Energies in Supramolecular Complexes," Chem. Rev. 2016, 116(9), 5216-5300 (85 pages).
Bock, Harald, et al. "Helicenes from Diarylmaleimides," Organic Letters 2014, 16, 1546-1549 (5 pages).
Boeseken, J. "The Use of Boric Acid for the Determination of the Configuration of Carbohydrates," Adv. Carbohydr. Chem. 1949, 4, 189-210 (22 pages).
Brust, Mathias, et al. "Novel Gold-Dithiol Nano-Networks with Non-Metallic Electronic Properties," Adv. Mater. 1995, 7, No. 9 795-797 (3 pages).
Brust, Mathias, et al. "Synthesis of Thiol-derivatised Gold Nanoparticles in a Two-phase Liquid-Liquid System," J. Chem. Soc., Chem. Commun., 1994, 801-802 (2 pages).

(56) References Cited

OTHER PUBLICATIONS

Cancilla, Devon A., et al. "O-(2,3,4,5,6-Pentafluorophenyl)methylhydroxylamine hydrochloride: a versatile reagent for the determination of carbonyl-containing compounds," Journal of Chromatography, 627 (1992) 1-16 (16 pages).
Cao, Mengmei, et al. "Electrochemical and Theoretical Study of π-π stacking Interactions between Graphitic Surfaces and Pyrene Derivatives," J. Phys. Chem. C 2014, 118(5), 2650-2659 (10 pages).
Capuano, Rosamaria, et al. "Corroles-Porphyrins: A Teamwork for Gas Sensor Arrays," Sensors, 2015, vol. 15, pp. 8121-8130 (10 pages).
Chen, Gugang, et al. "Sub-ppt gas detection with pristine graphene," Applied Physics Letters 101, 053119 (2012) 6 pages.
Cheng, Zengguang, et al. "Suspended Graphene Sensors with Improved Signal and Reduced Noise," Nano Lett. 2010, 10, 1864-1868 (5 pages).
Connors, Kenneth A., et al. "The Stability of Cyclodextrin Complexes in Solution," Chem. Rev. 1997, 97, 1325-1357 (34 pages).
Cui, Menghua, et al. "Graphene-organic two-dimensional charge transfer complexes: inter-molecular electronic transitions and broadband near infrared photoresponse," J. Phys. Chem. C 2018, 122 (13), 7551-7556 (7 pages).
Dreyer, Daniel, et al. "The chemistry of graphene oxide," Chem. Soc. Rev. 2010, 39(1), 228-240 (13 pages).
Elemans, Johannes A.A.W., et al. "Molecular Materials by Self-Assembly of Porphyrins, Phthalocyanines, and Perylenes," Adv. Mater. 2006, 18, 1251-1266 (16 pages).
Fan, Xuge, et al. "Humidity and CO2 gas sensing properties of double-layer graphene," Carbon 127 (2018) 576-587 (12 pages).
Fogel, Yulia, et al. "Graphitic Nanoribons with Dibenzo[e,l]pyrene Repeat Units: Synthesis and Self-Assembly," Macromolecules 2009, 42, 6878-6884 (7 pages).
Fuchs, Patricia, et al. "Breath gas aldehydes as biomarkers of lung cancer," Int. J. Cancer 2010, 126 (11), 2663-70 (8 pages).
Gao, Zhaoli, et al. "Scalable Production of Sensor Arrays Based on High-Mobility Hybrid Graphene Field Effect Transistors," ACS Applied Materials & Interfac. 2016, 8(41), 27546-27552 (8 pages).
Gautam, Madhav, et al. "Gas sensing properites of graphene synthesized by chemical vapor deposition," Materials and Science Engineering C31 (2011) 1405-1411 (7 pages).
Gavartin, J.L., et al. "The role of nitrogen-related defects in high-k dialectric oxides: Density-functional studies.," Journal of Applied Physics. (2005) vol. 97, Issue 5. (15 pages).
Geim, A.K., et al. "The rise of graphene," Nat. Mater. 2007, 6, 183-191 (9 pages).
Georgakilas, Vasilios, et al. "Functionalization of Graphene: Covalent and Non-Covalent Approaches, Derivatives and Applications," Chem. Rev. 2012, 112(11), 6156-6214 (59 pages).
Ghosh, Sujoy, et al. "Effect of 1-Pyrene Carboxylic-Acid Functionalization of Graphene on Its Capacitive Energy Storage," J. Phys. Chem. C 2012, 116, 20688-20693 (6 pages).
Giancane, Gabriele, et al. "State of Art in Porphyrin Langmuir-Blodgett Films as Chemical Sensors," Advances in Colloid and Interface Science, 2012, vol. 171-172, pp. 17-35 (Year: 2012), 19 pages.
Good, Robert J. "Contact angle, wetting, and adhesion: a critical review," J. Adhesion Sci. Technol. 1992, vol. 6, No. 12, pp. 1269-1302 (34 pages).
Gorodetsky, Alon A., et al. "Electrochemistry Using Self-assembled DNA Monolayers on Highly Oriented Pyrolytic Graphite," Langmuir 2006, 22, 7917-7922 (6 pages).
Guo, Zanru, et al. "Light-Switchable Single-Walled Carbon Nanotubes Based on Host-Guest Chemistry," Adv. Funct. Mater. 2013, 23, 5010-5018 (18 pages).
Hasobe, Taku "Photo- and Electro-Functional Self-Assembled Architectures of Porphyrins," Physics Chemistry Chemical Physics, 2012, 14, pp. 15975-15987 (Year: 2012), 13 pages.
Hayasaka, Takeshi, et al. "The influences of temperature, humidity, and O2 on electrical properties of graphene FETs," Sensors & Actuators: B. Chemical 285 (2019) 116-122 (7 pages).

Hill, Ernie W., et al. "Graphene Sensors," IEEE Sensors Journal, vol. 11, No. 12, Dec. 2011 (10 pages).
Hinnemo, Malkolm, et al. "On Monolayer Formation of Pyrenebutyric Acid on Graphene," Langmuir, 2017, vol. 33, No. 14 pp. 3588-3593 (6 pages).
Hockstein, Neil G., et al. "Diagnosis of Pneumonia with an Electronic Nose: Correlation of Vapor Signature with Chest Computed Tomography Scan Findings," The Laryngoscope 2004, 114 (10), 1701-1705 (5 pages).
Hong Chan, Wing, et al. "Optodes based on a calixarene ester for the determination of aldehydes via in situ generation of the Girard's reagent P derivative," Analyst 1998, 123 (12), 2851-2856 (6 pages).
Hsiao, Min-Chien, et al. "Preparation and properties of a graphene reinforced nanocomposite conducting plate," J. Mater. Chem., 2010, 20, 8496-8505 (10 pages).
Hsieh, Chien-Te. et al. "Field emission from various CuO nanostructures," Applied Physics Letters 2003, vol. 83, No. 6 (3 pages).
Huang, Ke-Jing,et al. "Novel electrochemical sensor based on functionalized graphene for simultaneous determination of adenine and guanine in DNA," Colloids and Surfaces B: Biointerfaces 82 (2011) 543-549 (7 pages).
Hunter, Christopher A., et al. "The Nature of π-π Interactions," J. Am. Chem. Soc. 1990, 112, 5525-5534 (10 pages).
Hwang, Michael, et al. "Ultrasensitive detection of nucleic acids using deformed graphene channel field effect biosensors," Nat. Commun. 2020, 11(1) (11 pages).
Iezhokin, I., et al. "Porphyrin molecules boost the sensitivity of epitaxial graphene for NH3 detection," J. Phy.: Condens. Matter 29 (2017) (11 pages).
Ionescu, Radu, et al. "Detection of Multiple Sclerosis from exhaled Breath Using Bilayers of Polycyclic Aromatic Hydrocarbons and Single-Wall Carbon Nanotubes," ACS Chemical Neurosci. 2011, 2(12), 687-693 (7 pages).
Jiao, Dezhi, et al. "Supramolecular Peptide Amphiphile Vesicles through Host-Guest Complexation," Angew. Chem. Int. Ed. 2012, 51, 9633-9637 (5 pages).
Kang, Junmo, et al. ."Graphene Transfer: key for applications," Nanoscale, 2012, 4, 5527 (11 pages).
Kang, Xinhuang, et al. "Glucose Oxidase-graphene-chitosan modified electrode for direct electrochemistry and glucose sensing," Biosensors and Bioelectronics 25 (2009) 901-905 (5 pages).
Knipp, Ralph J., et al. "A versatile probe for chemoselective capture and analysis of carbonyl compounds in exhaled breath," Anal Methods, 2015, 7, 6027 (7 pages).
Kobayashi, Keiko, et al. "Gas chromatrographic determination of low-molecular-weight carbonyl compounds in aqueous solution as their O-(2,3,4,5,6-pentafluorobenzyl) oximes," Journal of Chromatography A 1980, 187(2), 413-417 (5 pages).
Kozbial, Andrew, et al. "Study on the surface energy of graphene by contact angle measurement," Langmuir 2014, 30 (28), 8598-8606 (28 pages).
Kuila, Tapas, et al. "Chemical functionalization of graphene and its applications," Progress in Materials Science 57 (2012) 1061-1105 (45 pages).
Lauffer, Peter, et al. "Molecular and electronic structure of PTCDA on bilayer graphene on SiC(0001) studied with scanning tunnerling microscopy," Phys. Stat. Sol. (b) 2008, 245, No. 10, 2064-2067 (4 pages).
Lechner, Christoph, et al. "Adhesive Forces Between Aromatic Molecules and Graphene," The Journal of Physical Chemistry C 2014, 118(36), 20970-20981 (12 pages).
Lecourt, Thomas, et al. "Triisobutylaluminium and Diisobutylaluminium Hydride as Molecular Scalpels: The Regioselective Stripping of Perbenzylate Sugars and Cyclodextrins," Chem. Eur. J. 2004, 10, 2960-2971 (12 pages).
Li, Errui, et al. "Aliphatic Aldehyde Detection and Adsorption by Nonporous Adaptive Pillar[4]arene[1]quinone Crystals with Vapochromic Behavior," ACS Applied Materials & Interfaces, 2018, 10, 23147-23153 (23 pages).
Li, Mingxiao, et al. "Preconcentration and Analysis of Trace Volatile Carbonyl Compounds," Anal Chem 2012, 84(3), 1288-1293 (6 pages).

(56) References Cited

OTHER PUBLICATIONS

Lienerth, Peter, et al. "Improving the Selectivity to Polar Vapors of OFET-Based Sensors by Using the TranfserCharactersitics Hysteresis Response," Sensors and Actuators B 225 (2016) 90-95 (6 pages).

Liu, Sophie F., et al. "Single-walled Carbon Nanotube-Metalloporphyrin Chemiresistive Gas Sensor Arrays for Volatile Organic Compounds," Chemistry of Materials, vol. 27, No. 10 (2015) pp. 3560-3563 (5 pages).

Liu, Yifei M., et al. "Electrochemical Sensing of Nitric Oxide with Functionalized Graphene Electrodes," ACS Applied Materials & Interfaces 2013, 5(23), 12624-12630 (7 pages).

Liu, Yuxin, et al. "Biological and Chemical Sensors based on Graphene Materials," Chem. Soc. Rev. 2012, 41 (6), 2283-2307 (27 pages).

Loh, Kian Ping, et al. "The Chemistry of Graphene," J. Mater. Chem., 2010, 20, 2277-2289 (13 pages).

Long, Brenda, et al. "Non-Covalent Functionalization of Graphene Using Self-Assembly of Alkane-Amines," Adv. Funct. Mater. 2012, 22, 717-725 (9 pages).

Lu, Chun-Hua, et al. "A Graphene Platform for Sensing Biomolecules," Angew. Chem. Int. Ed. 2009, 48, 4785-4787 (3 pages).

Mackin, Charles, et al. "Chemiresistive Graphene Sensors for Ammonia Detection," ACS Appl. Mater. Interfaces 2018, 10, 16169-16176 (8 pages).

Mann, Jason A., et al. "Improving the Binding Characteristics of Tripodal Compounds on Single Layer Graphene," American Chemical Society 2013, vol. 7, No. 8, 7193-7199 (7 pages).

Manochehry, Sepehr, et al. "Optical biosensors utilizing graphene and functional DNA molecules," J. Mater. Res. 2017, 32(15), 2973-2983 (11 pages).

Manolis, Antony "The Diagnostic Potential of Breath Analysis," Clin. Chem. 29/1, 5-15 (1983) (11 pages).

Mao, Shun, et al. "Specific Protein Detection Using Thermally Reduced Graphene Oxide Sheet Decorated with Gold Nanoparticle-Antibody Conjugates," Adv. Mater. 2010, 22, 3521-3526 (6 pages).

McCulloch, Michael, et al. "Diagnostic Accuracy of Canine Scent Detection in Early-and Late-Stage Lung and Breast Cancers," Integrative Cancer Therapies 2006, 5(1), 30-39 (11 pages).

Moldoveanu, Serban C., et al. "Derivatization Methods in GC and GC/MS," in Gas Chromatography-Derivatization, Sample Preparation, Application, Kusch, P., Ed. IntechOpen:2018 (33 pages).

Muruganathan, Manoharan, et al. "Electrically Tunable van der Waals Interaction in Graphene-Molecule Complex," Nano Lett. 2015, 15(12), 8176-8180 (5 pages).

Nag, Sanada, et al. "Ultrasensitive QRS made by supramolecular assembly of functionalized cyclodextrins and graphene for the detection of lung cancer VOC biomarkers," Journals of Materials Chemistry B 2014, 2, pp. 6571-6579 (9 pages).

Novoselov, K.S., et al. "Electric Field Effect in Atomically Thin Carbon Films," Science 2004, 306, 666-669 (5 pages).

Ohno, Yasuhide, et al. "Electrolyte-Gated Graphene Field-Effect Transistors for Detecting pH and Protein Adsorption," Nano Letters 2009, vol. 9, No. 9, 3318-3322 (5 pages).

Olson, Eric J., et al. "Getting More out of a Job Plot: Determination of Reactant to Product Stoichiometry in Cases of Displacement Reactions and n:n Complex Formation," J. Org. Chem. 2011, 76, 8406-8412 (7 pages).

Ou, Baoli, et al. "Covalent functionalization of graphene with poly(methyl methacrylate) by atom transfer radical polymerization at room temperature," Polym. Chem., 2012, 3, 2768 (8 pages).

Park, Eun Uk, et al. "Correlation between the sensitivity and the hysteresis of humidity sensors based on graphene oxides," Sensors and Actuators B 258 (2018) 255-262 (8 pages).

Pathipati, Srinivasa Rao, et al. "Modulation of charge transport properties of reduced graphene oxide by submonolayer physisorption of an organic dye," Organic Electronics 14 (2013) 1787-1792 (6 pages).

Peng, Gang, et al. "Diagnosing lung cancer in exhaled breath using gold nanoparticles," Nature nanotechnology, 2009, 4(10), 669-673 (5 pages).

Peressi, Maria "Surface Functionalization of Graphene," Graphene Chemistry, John Wiley & Sons, Ltd:2013, pp. 233-253 (21 pages).

Poli, Diana, et al. "Determination of aldehydes in exhaled breath of patients with lung cancer by means of on-fiber-derivatisation SPME-GC/MS," Journal of Chromatography B, 878 (2010) 2643-2651 (9 pages).

Poulston, S., et al. "Surface Oxidation and Reduction of CuO and Cu2O Studied Using XPS and XAES," Surface and Interface Analysis, vol. 24, 811-820, 1996, (10 pages).

Pyo, Soonjae, et al. "Improved photo- and chemical-responses of graphene via porphyrin-functionalization for flexible, transparent, and sensitive sensors," Nanotechnology 30 (2019) 215501 (9 pages).

Rekharsky, Mikhail V., et al. "Complexation Thermodynamics of Cyclodextrins," Chem. Rev. 1998, 98, 1875-1917 (44 pages).

Reuillard, B., et al. "Non-covalent double functionalization of carbon nanotubes wiht a NADH oxidation Ru(II)-based molecular catalyst and a NAD-dependent glucose dehydrogenase," Chem. Commun. 2014, 50(79), 11731-11734 (5 pages).

Rodner, Marius, et al. "Graphene Decorated with Iron Oxide Nanoparticles for Highly Sensitive Interaction with Volatile Organic Compounds," Sensors 2019, 19, 918-026 (9 pages).

Rushi, A.D., et al. "Exercising Substituents in porphyrins for real time selective sensing of volatile organic compounds," Sensors and Actuators B: Chemical, vol. 257, 2018, pp. 389-397 (9 pages).

Schedin, F., et al. "Detection of Individual Gas Molecules Adsorbed on Graphene," Nat. Mater. 2007, 6(9), 652-655 (11 pages).

Shao, Yuyan "Graphene Based Electrochemical Sensor and Biosensors: A Review," Electroanalysis 2010, 22, No. 10, 1027-1036 (10 pages).

Shao, Yuyan, et al. "Nitrogen-doped graphene and its electrochemical applications," J. Mater. Chem., 2010, 20, 7491-7496 (6 pages).

Song, Nan, et al. "Applications of pillarenes, an emerging class of synthetic macrocycles," Science China Chemistry, 2014, 57(9), 1185-1198 (15 pages).

Su, Qun, et al. "Understanding Sources of Electrical Disorder in Graphene Grown by Chemical Vapor Deposition for Wafer-Scale Device Applications," ACS Appl. Nano Mater., vol. 2 (2019) 3426-3433 (26 pages).

Suk, Ji Won, et al. "Transfer of CVD-Grown Monolayer Graphene onto Arbitrary Substrates," ACS Nano 2011, 5(9), 6916-6924 (10 pages).

Swanson, Emily, et al. "Self Assembly of Monolayers on Graphene with Pyrene and Cyclodextrin Derivatives," Research Poster. Elon University, LANDO program, Research Experience for Undergraduates Program of the National Science Foundation, Council of Undergraduate Research Experiences for Undergraduates symposium in Washington, D.C., Oct. 23-24, 2016 (1 page).

Szejtli, Jozef "Introduction and General Overview of Cyclodextrin Chemistry," Chem. Rev. 1998, 98, 1743-1753 (12 pages).

Terse-Thakoor, Trupti, et al. "Graphene based biosensors for healthcare," J. Mater. Res. 2017, 32(15), 2905-2929 (25 pages).

Turkevich, John, et al. "A study of the nucleation and growth processes in the synthesis of colloidal gold," Discuss. Faraday Soc., 1951,11, 55-75 (23 pages).

Vincent, Mark A., et al. "Accurate Prediction of Adsorption Energies on Graphene, Using a Dispersion-Corrected Semiempirical Method Including Solvation," J. Chem. Inf. Model. 2014, 54, 2225-2260 (6 pages).

Wang, Lihua "A novel [beta]-cyclodextrin Functionalized Reduced Graphene Oxide Electrochemical Sensor for Blood Glucose Detection," International Journal of Electrochemical Science, Dec. 28, 2017 pp. 1594-1602 (9 pages).

Wang, Qing Hua, et al. "Room-temperature molecular-resolution characterization of self-assembled organic monolayers on epitaxial graphene," Nature Chemistry 2009 vol. 1 (3), 206-211 (6 pages).

Wei, Jinwei, et al. "Understanding asymmetric transfer characteristics and hysteresis behaviors in graphene devices under different chemical atmospheres," Carbon 156 (2020) 67-76 (10 pages).

(56) References Cited

OTHER PUBLICATIONS

Wu, Ting, et al. "Quantitative principles for precise engineering of sensitivity in carbon-based electrochemical sensors," Adv. Mater. 2018, 1805752 (27 pages).

Xu, Huifeng, et al. "Direct Electrochemixtry and electrocatalysis of hemoglobin protein entrapped in graphene and chitosan composite film," Talanta 81 (2010) 334-338 (5 pages).

Xu, Mengjian, et al. "Gate-polarity-dependent doping effects of H2O adsorption on graphene/SiO2 field-effect transistors," J. Phys. D: Appl. Phys. 53 455301, 2020, (8 pages).

Xu, Shicai, et al. "Real-time reliable determination of binding kinetics of DNA hybridization using a multi-channel graphene biosensor," Nat. Commun. 2017, 8(1) 11 pages.

Xu, Yuxi, et al. "Flexible Graphene Films via te Filtration of Water-Soluble Noncovalent Functionalized Graphene Sheets," J. Am. Chem. Soc. 2008, 130, 5856-5857 (2 pages).

Yavari, Fazel, et al. "Graphene-Based Chemical Sensors," J. Phys. Chem. Lett. 2012, 3, 1746-1753 (8 pages).

Yildiz, Ibrahim "A DFT Approach to the Mechanistic Study of Hydrozone Hydrolysis," J. Phys. Chem. A 2016, 120 (20), 3683-92 (25 pages).

Zhang, Yiheng, et al. "Direct Measurements of the Interaction between Pyrene and Graphite in Aqueous Media by Single Molecule Force Spectroscopy Understanding the $\pi$-$\pi$ Interactions," Langmuir 2007, 23, 7911-7915 (5 pages).

Zhao, Yan-Li, et al. "Noncovalent Functionalization of Single-Walled Carbon Nanotubes," Accounts of Chemical Research 2009, vol. 42, No. 8. 1161-1171 (12 pages).

Zheng, Peiru, et al. "Oxidation of graphene with variable defects: alternately symmetrical escape and self-restructuring of carbon rings," Nanoscale 2020, 12 (18), 10140-10148 (10 pages).

Zhu, Congzhi, et al. "Mingling Electronic Chemical Sensors with Supramolecular Host-Guest Chemistry," Current Organic Chemistry, 2014, 18, 1957-1964 (8 pages).

Zhu, Yanwu, et al. "Graphene and Graphene Oxide: Synthesis, Properties, and Applications," Adv. Mater. 2010, 22, 3906-3924 (19 pages).

"Response to Non-Final Rejection," dated Jun. 20, 2022 for U.S. Appl. No. 16/696,348, submitted via EFS-Web on Sep. 20, 2022, 9 pages.

"Final Office Action," for U.S. Appl. No. 16/696,348 dated Nov. 3, 2022 (39 pages).

"Non-Final Office Action," for U.S. Appl. No. 17/101,900 dated Nov. 4, 2022 (19 pages).

"Response to Communication Pursuant to Article 94(3) EPC," for European Patent Application No. 15790739.5 filed Oct. 12, 2022 (35 pages).

\* cited by examiner

US 11,662,325 B2

1

SYSTEMS AND METHODS FOR MEASURING KINETIC RESPONSE OF CHEMICAL SENSOR ELEMENTS

This application claims the benefit of U.S. Provisional Application No. 62/781,254, filed Dec. 18, 2018, the content of which is herein incorporated by reference in its entirety.

FIELD

Embodiments herein relate to systems and methods for kinetic response sensing of gaseous mixtures using a chemical sensor element.

BACKGROUND

The accurate detection of diseases can allow clinicians to provide appropriate therapeutic interventions. The early detection of diseases can lead to better treatment outcomes. Diseases can be detected using many different techniques including analyzing tissue samples, analyzing various bodily fluids, diagnostic scans, genetic sequencing, and the like.

Some disease states result in the production of specific chemical compounds. In some cases, volatile organic compounds (VOCs) released into a gaseous sample of a patient can be hallmarks of certain diseases. The detection of these compounds or differential sensing of the same can allow for the early detection of particular disease states. However, mixtures of complex gases can be difficult to distinguish from one another with current detection methods.

SUMMARY

In a first aspect, a kinetic response system for measuring analyte presence on a chemical sensor element is included. The chemical sensor element can include one or more discrete binding detectors, where each discrete binding detector can include a graphene varactor. The kinetic response system can include a measurement circuit including an excitation voltage generator configured to generate a series of excitation cycles over a time period, where each excitation cycle includes delivering a DC bias voltage to the discrete binding detectors at multiple discrete DC bias voltage values across a range of DC bias voltages. The kinetic response system can include a capacitance sensor configured to measure capacitance of the discrete binding detectors resulting from the excitation cycles. The kinetic response system can include a controller circuit configured to determine the kinetics of change in at least one of a measured capacitance value and a calculated value based on the measured capacitance over the time period.

In a second aspect, in addition to one or more of the preceding or following aspects, or in the alternative to some aspects, the controller circuit is configured to calculate a rate of change of a measured capacitance or a calculated value based on measured capacitance over the time period at multiple discrete DC bias voltages.

In a third aspect, in addition to one or more of the preceding or following aspects, or in the alternative to some aspects, the controller circuit is configured to calculate an average rate of change of measured capacitance over the time period at multiple discrete DC bias voltages.

In a fourth aspect, in addition to one or more of the preceding or following aspects, or in the alternative to some aspects, the controller circuit is configured to determine the start of a steady-state response phase from each of the discrete binding detectors by assessing a rate of change of measured capacitance over the time period.

In a fifth aspect, in addition to one or more of the preceding or following aspects, or in the alternative to some aspects, the controller circuit is configured to determine the start of a non-steady state response phase from each of the discrete binding detectors by assessing a rate of change of measured capacitance over the time period.

In a sixth aspect, in addition to one or more of the preceding or following aspects, or in the alternative to some aspects, the controller circuit is configured to determine the end of the non-steady state response phase from each of the discrete binding detectors by assessing a rate of change of measured capacitance over the time period. The profile of the measured capacitance during the non-steady state response phase for each discrete binding detector can define a unique kinetic response profile for a unique gaseous mixture.

In a seventh aspect, in addition to one or more of the preceding or following aspects, or in the alternative to some aspects, the controller circuit is configured to calculate the rate of change in the Dirac point for the discrete binding detectors over the time period.

In an eighth aspect, in addition to one or more of the preceding or following aspects, or in the alternative to some aspects, the controller circuit is configured to determine a maximum rate of change for capacitance for the discrete binding detectors over the time period.

In a ninth aspect, in addition to one or more of the preceding or following aspects, or in the alternative to some aspects, the kinetic response system can include a nonvolatile memory configured to store measured capacitance values for the discrete binding detectors across the range of DC bias voltages.

In a tenth aspect, in addition to one or more of the preceding or following aspects, or in the alternative to some aspects, the kinetic response system can include a nonvolatile memory configured to store a baseline capacitance for the discrete binding detectors across the range of DC bias voltages.

In an eleventh aspect, in addition to one or more of the preceding or following aspects, or in the alternative to some aspects, each of the plurality of discrete binding detectors has a different surface chemistry.

In a twelfth aspect, in addition to one or more of the preceding or following aspects, or in the alternative to some aspects, each of the plurality of discrete binding detectors has the same surface chemistry.

In a thirteenth aspect, in addition to one or more of the preceding or following aspects, or in the alternative to some aspects, the kinetic response system can include a flow control valve in fluid communication with an upstream flow path relative the chemical sensor element.

In a fourteenth aspect, a method for measuring analyte presence on a chemical sensor element using a kinetic response system is included. The method can include contacting a chemical sensor element including one or more discrete binding detectors with a gaseous mixture, each discrete binding detector including a graphene varactor. The method can include generating a series of excitation cycles over a time period, wherein each excitation cycle includes delivering a DC bias voltage to the graphene varactor at multiple discrete DC bias voltage values across a range of DC bias voltages. The method can include measuring capacitance of each of the discrete binding detectors resulting from the excitation cycles. The method can include determining the kinetics of change in at least one of a measured capacitance value and a calculated value based on the measured capacitance over the time period.

In a fifteenth aspect, in addition to one or more of the preceding or following aspects, or in the alternative to some aspects, the method can include calculating a rate of change of a measured capacitance or a calculated value based on measured capacitance over the time period.

In a sixteenth aspect, in addition to one or more of the preceding or following aspects, or in the alternative to some aspects, the method can include calculating an average rate of change of measured capacitance over the time period at multiple discrete DC bias voltages.

In a seventeenth aspect, in addition to one or more of the preceding or following aspects, or in the alternative to some aspects, the method can include determining the start of a steady-state response phase from each of the discrete binding detectors by assessing a rate of change of measured capacitance over the time period.

In an eighteenth aspect, in addition to one or more of the preceding or following aspects, or in the alternative to some aspects, the method can include determining the start of a non-steady state response phase from each of the discrete binding detectors by assessing a rate of change of measured capacitance over the time period.

In a nineteenth aspect, in addition to one or more of the preceding or following aspects, or in the alternative to some aspects, the method can include determining the end of the non-steady state response phase from each of the discrete binding detectors by assessing a rate of change of measured capacitance over the time period, where the start of the non-steady state response phase and the end of the non-steady state response phase for the discrete binding detectors defines a unique kinetic response profile for a unique gaseous mixture.

In a twentieth aspect, in addition to one or more of the preceding or following aspects, or in the alternative to some aspects, the method can include distinguishing one unique gaseous mixture from another unique gaseous mixture based on the unique kinetic response profile of the unique gaseous mixtures.

In a twenty-first aspect, in addition to one or more of the preceding or following aspects, or in the alternative to some aspects, the method can include calculating the rate of change in the Dirac point for the discrete binding detectors over the time period.

In a twenty-second aspect, in addition to one or more of the preceding or following aspects, or in the alternative to some aspects, the method can include contacting the chemical sensor element with a gas other than a sample gas and detecting a return of each of the discrete binding detectors back toward a baseline capacitance valve.

In a twenty-third aspect, in addition to one or more of the preceding or following aspects, or in the alternative to some aspects, delivering a DC bias voltage across a range of DC bias voltages is conducted from −3 V to 3 V.

In a twenty-fourth aspect, in addition to one or more of the preceding or following aspects, or in the alternative to some aspects, delivering a DC bias voltage to the graphene varactor at multiple discrete DC bias voltage values across a range of DC bias voltages includes stepping through the range of DC bias voltages in 50 mV increments.

In a twenty-fifth aspect, in addition to one or more of the preceding or following aspects, or in the alternative to some aspects, delivering a DC bias voltage to the graphene varactor at multiple discrete DC bias voltage values across a range of DC bias voltages includes stepping through the range of DC bias voltages in 10 mV increments.

In a twenty-sixth aspect, in addition to one or more of the preceding or following aspects, or in the alternative to some aspects, at least 100 measured capacitance values are stored into memory for each discrete binding detector across the range of DC bias voltages.

In a twenty-seventh aspect, in addition to one or more of the preceding or following aspects, or in the alternative to some aspects, the time period for generating a series of excitation cycles comprises from 30 seconds to 1200 seconds.

In a twenty-eighth aspect, in addition to one or more of the preceding or following aspects, or in the alternative to some aspects, the time period for each excitation cycle comprises from 1 second to 30 seconds.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
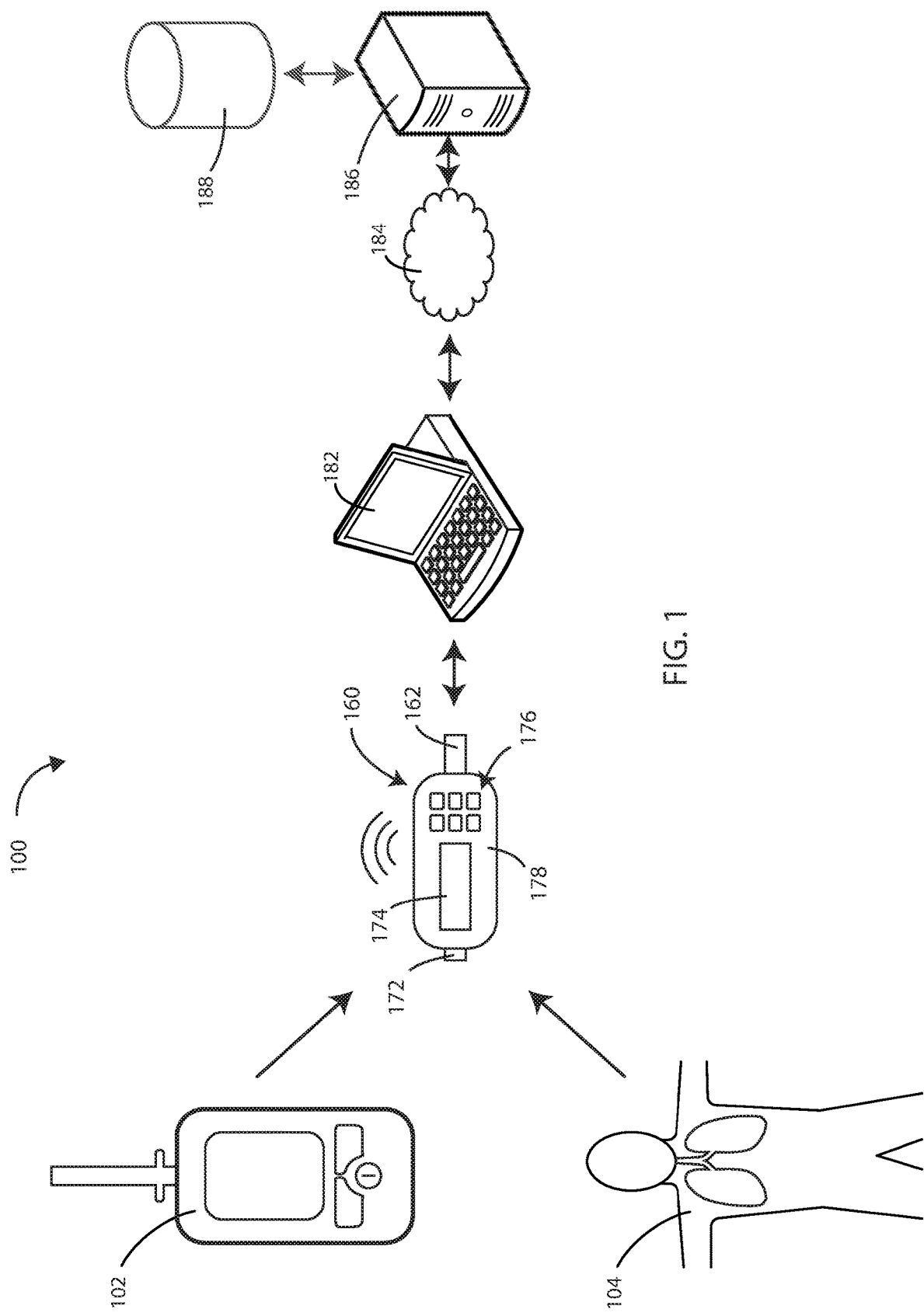
FIG. 1 is a schematic view of various components of a system in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Chemical sensor elements having one or more discrete binding detectors can be configured to bind one or more analytes, such as volatile organic compounds (VOCs), in a complex gaseous mixture. The discrete binding detectors can include graphene quantum capacitance varactors ("graphene varactors") that can exhibit a change in capacitance in response to an applied bias voltage as a result of the presence of one or more analytes, such as volatile organic compounds (VOCs) on a surface of the graphene varactor. In this way, gas samples can be analyzed by contacting them with a graphene varactor-based sensor element, providing a bias voltage, and measuring capacitance. In many cases, the graphene varactor-based sensor elements can be exposed to a range of bias voltages in order to discern features such as the Dirac point (or the bias voltage at which the varactor exhibits the lowest capacitance). The response signal generated by the discrete binding detectors in the presence or absence of one or more analytes can be used to characterize the content of the gaseous mixture. As such, each gaseous mixture will have a unique set of response signals, or "fingerprint," for any given array.

Frequently, measurements of capacitance can be thought of as being performed at "steady-state" points in time where values for capacitance are not changing substantially. Exemplary steady-state points in time herein can include a starting state (such as before the graphene varactor is exposed to a gas sample) and an ending state (such as when the graphene varactor has been exposed to a gas sample sufficiently long to exhibit steady values or "plateaued values" for capacitance in response to bias voltages).

However, it has been discovered that measuring capacitance values at times falling between steady-state points in time (such as while capacitance values are changing after initial exposure to a gas sample and before it starts to exhibit steady values for capacitance) can provide substantial additional data for enhanced resolution of gas samples. This is because in some scenarios the capacitance values at a starting state and an ending state for two different gas samples may be extremely similar or the same. Thus, using only data reflecting the steady-state points in time may not be sufficient to distinguish between such gas samples. But the way in which the capacitance values change between steady-state points in time (e.g., the kinetics of the change between a starting state and an ending state) may be quite different. As such, in accordance with various embodiments herein, the kinetics of capacitance value change are measured and recorded to aid in the analysis of gaseous samples.

Referring now to FIG. 1, a schematic view is shown of components of a kinetic response system 100 in accordance with various embodiments herein. The kinetic response system 100 can include a sensing device 160 including a chemical sensor element including one or more graphene varactors for sensing analytes in a gaseous mixture. The graphene varactors suitable for use herein will be discussed in more detail in reference to FIGS. 8-11 below. In the embodiment shown in FIG. 1, the sensing device 160 of kinetic response system 100 is depicted in a hand-held format that can be used in the field. However, it will be appreciated that many other formats for the sensing device 160 and kinetic response system 100 are contemplated herein.

The sensing device 160 can include a housing 178 and an air intake port 162. In some embodiments, air intake port 162 can be in fluid communication with one or more gas sampling devices 102. In other embodiments, air intake port 162 can be configured as a mouthpiece into which a subject 104 to be evaluated can blow a breath sample. In yet other embodiments, the air intake port 162 can itself act as a gas sampling device. The sensing device 160 can be configured to actively draw a gas into housing 178 or it can be configured to receive a gas passively from a subject 104 or a gas sampling device 102. In some embodiments, the sensing device 160 can include a flow control valve in fluid communication with an upstream flow path relative the chemical sensor element.

The sensing device 160 can also include a display screen 174 and a user input device 176, such as a keyboard. The sensing device 160 can also include a gas outflow port 172. Aspects of sensing systems and devices are described in U.S. Patent Application Publication No. 2016/0109440A1, the content of which is herein incorporated by reference. While FIG. 1 shows a sensing device 160 adapted to receive gas from a subject or gas sampling device, it will be appreciated that other types of gas sampling systems can also be used herein. For example, gas sampling devices for use with catheters and endoscopy systems can also be used. An exemplary gas sampling device in the context of a catheter or endoscopy device is described in U.S. Patent Application Publication No. 2017/0360337A1, the content of which is herein incorporated by reference.

In some embodiments, the kinetic response system 100 can include a local computing device 182 that can include a microprocessor, input and output circuits, input devices, a visual display, a user interface, and the like. In some embodiments, the sensing device 160 can communicate with the local computing device 182 in order to exchange data between the sensing device 160 and the local computing device 182. The local computing device 182 can be configured to perform various processing steps with the data received from the sensing device 160, including, but not limited to, calculating various parameters of the graphene varactors described herein. However, it should be appreciated that in some embodiments the features associated with the local computing device 182 can be integrated into the sensing device 160. In some embodiments, the local computing device 182 can be a laptop computer, a desktop computer, a server (real or virtual), a purpose dedicated computer device, or a portable computing device (including, but not limited to, a mobile phone, tablet, wearable device, etc.).

The local computing device 182 and/or the sensing device 160 can communicate with computing devices in remote locations through a data network 184, such as the Internet or another network for the exchange of data as packets, frames, or otherwise.

In some embodiments, the kinetic response system 100 can also include a computing device such as a server 186 (real or virtual). In some embodiments, the server 186 can be located remotely from the sensing device 160. The server 186 can be in data communication with a database 188. The database 188 can be used to store various subject information, such as that described herein. In some embodiments, the database can specifically include an electronic medical database containing data regarding the health status of a subject, patterns of data associated with various conditions (such as that generated from machine learning analysis of large sets of subject data), demographic data and the like. In some embodiments, the database 188 and/or server 186, or a combination thereof, can store the data generated by the chemical sensor elements(s) as well as data output generated by machine learning analysis.

Each chemical sensor element within the kinetic response system can include one or more discrete binding detectors in an array. The terms "discrete binding detector" and "graphene varactor" can be used interchangeably herein unless otherwise specified or the context dictates otherwise. Each discrete binding detector can include a graphene varactor that can produce a response signal before exposure to a gaseous mixture and a response signal after exposure to a gaseous mixture. To generate a response signal, an excitation current at a particular voltage and/or over a range of voltages is delivered to the graphene varactor(s) over a given time period. Measuring the response signal, such as the measuring the capacitance, provides data that reflects the binding status of analytes to the graphene varactor(s) or the baseline response of a graphene varactor with no bound analytes.

Figure 2:
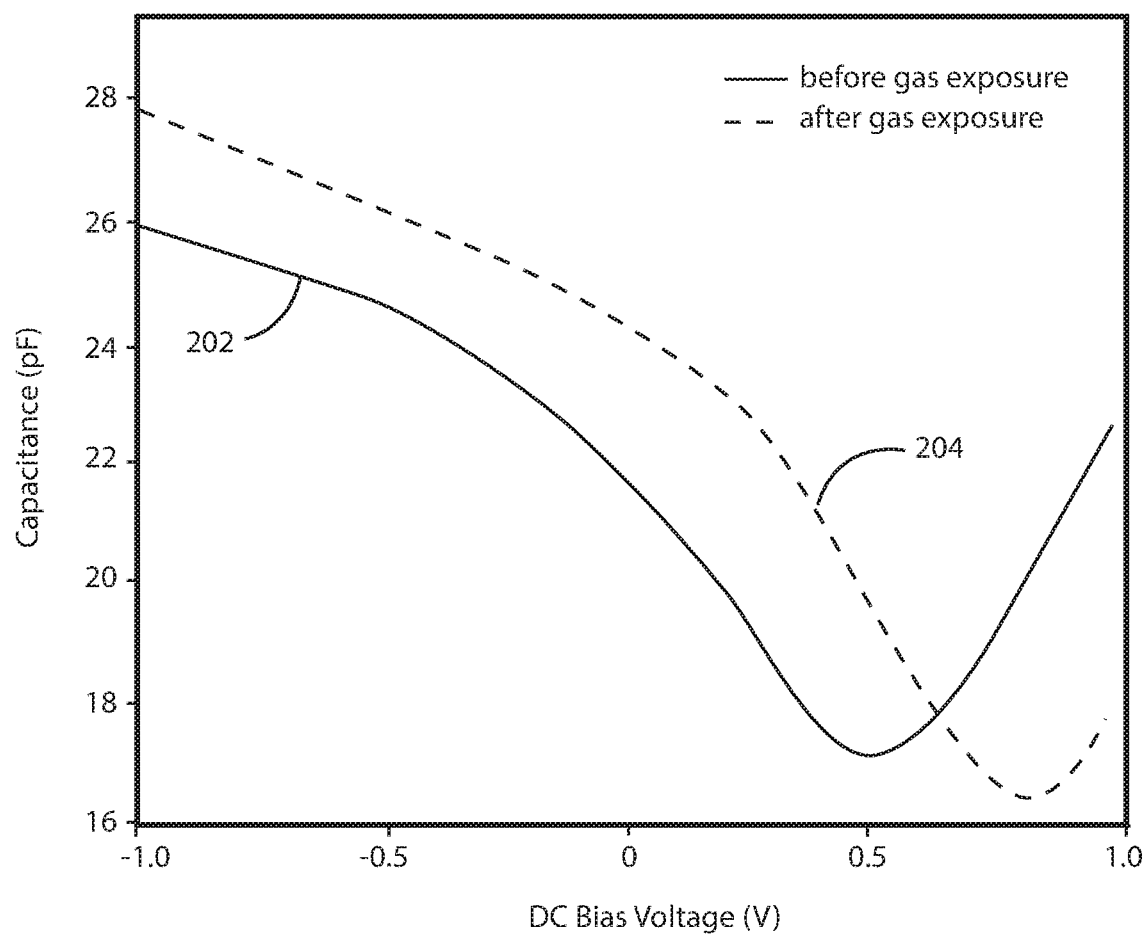
FIG. 2 is a graph showing capacitance versus DC bias voltage for a graphene varactor in accordance with various embodiments herein.

When a graphene varactor is exposed to a gaseous mixture the response signal can change when compared to the baseline response signal in the absence of a gaseous mixture. Referring now to FIG. 2, response signals for an individual graphene varactor before and after exposure to an example gaseous mixture are shown on a graph of capacitance versus DC bias voltage in accordance with various embodiments herein. The response signal for the graphene varactor before exposure to a gaseous mixture is shown in plot 202. The response signal for the same graphene varactor after exposure to a gaseous mixture is shown in plot 204. Response signals, such the capacitance versus voltage curve shown in FIG. 2, can be established by measuring capacitance over a range of DC bias voltages (an example of an excitation cycle), both before and after exposing a graphene varactor to a gaseous mixture.

Figure 3:
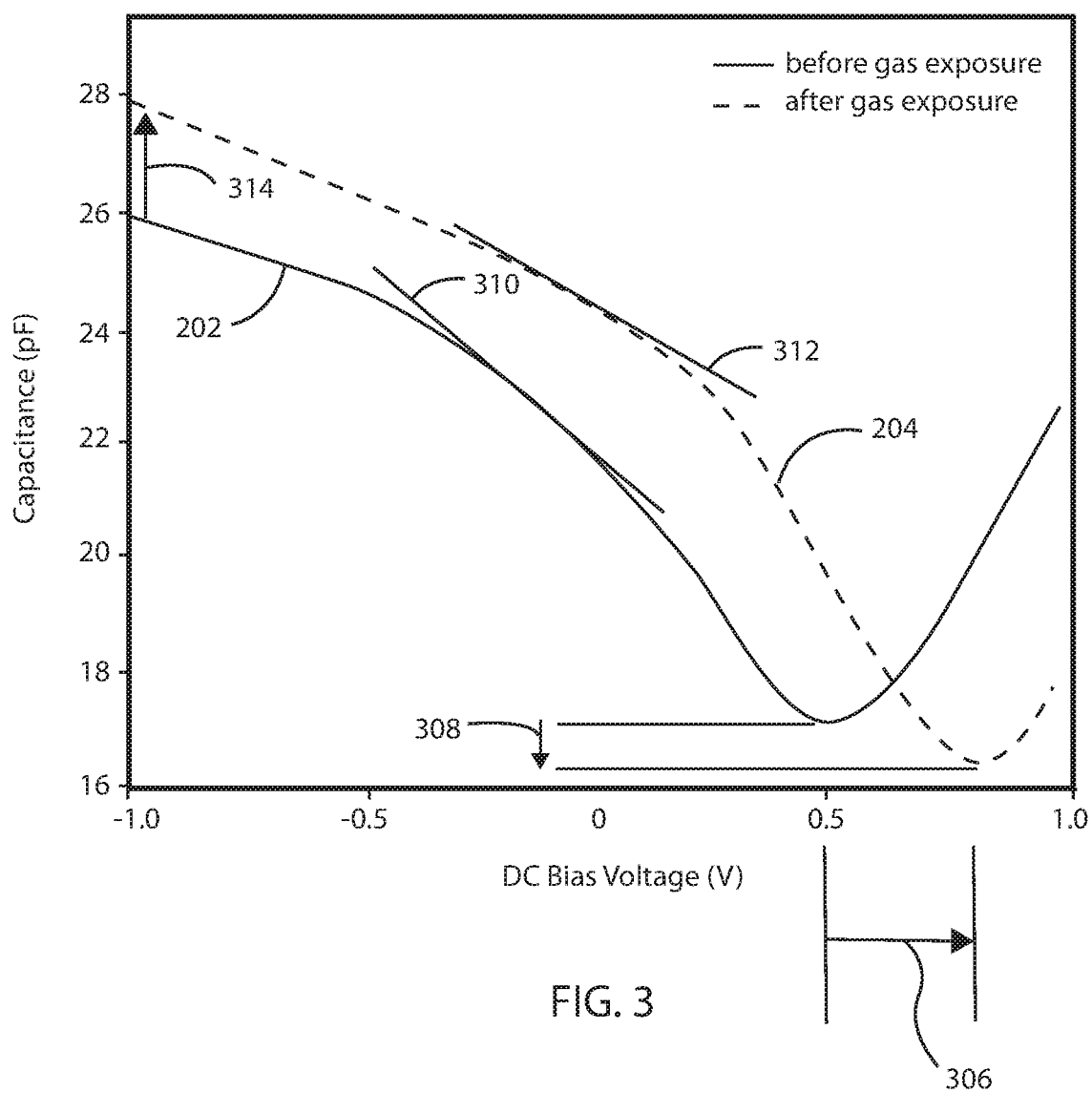
FIG. 3 is a graph showing capacitance versus DC bias voltage for a graphene varactor in accordance with various embodiments herein.

As analytes within the gaseous mixture are sensed by the graphene varactors upon binding, several different parameters of the graphene varactor response signal can change from a baseline value to a higher or a lower value, and the shape of the response signal can change. Referring now to FIG. 3, the same response signals for an individual graphene varactor before and after exposure to a gaseous mixture are shown that were shown in FIG. 2, but with various annotations provided to highlight the change in the different parameters of the graphene varactor response signal that can be analyzed to characterize the content of a gaseous mixture. By way of example, these different parameters can include, but are not to be limited to, a shift in the Dirac point (i.e., the voltage when the capacitance of a graphene varactor is at a minimum), a change in the minimum capacitance of the graphene varactor, a change in the slope of the response signal, or the change in the maximum capacitance of the graphene varactor, change in capacitance at a particular bias voltage, or the like (other examples of parameters are described below).

In FIG. 3, the response signal for the graphene varactor before exposure to a gaseous mixture is shown as plot 202, while the response signal for the same graphene varactor after exposure to a gaseous mixture is shown as plot 204. The shift in the Dirac point is indicated as arrow 306. The change in the minimum capacitance of the graphene varactor is indicated as arrow 308. The change in the slope of the response signal can be obtained by comparison of the slope 310 of plot 202 for the graphene varactor before exposure to a gaseous mixture with the slope 312 of plot 204 for the graphene varactor after exposure to a gaseous mixture. The change in the maximum capacitance of the graphene varactor is indicated as arrow 314.

In some embodiments, a ratio of the maximum capacitance to minimum capacitance can be used to characterize the content of a gaseous mixture. In some embodiments, a ratio of the maximum capacitance to the shift in the Dirac point can be used to characterize the content of a gaseous mixture. In other embodiments, a ratio of the minimum capacitance to the shift in the slope of the response signal can be used to characterize the content of a gaseous mixture. In some embodiments, a ratio of any of the parameters including a shift in the Dirac point, a change in the minimum capacitance, a change in the slope of the response signal, or the change in the maximum capacitance can be used to characterize the content of a gaseous mixture.

The two plots in FIGS. 2 and 3 can represent "steady-state" points in time where values for capacitance are not changing substantially, such as a starting state (such as before the graphene varactor is exposed to a gas sample) and an ending state (such as when the graphene varactor has been exposed to a gas sample sufficiently long to exhibit steady values for capacitance in response to bias voltages).

However, in accordance with various embodiments, a series of response signals or response curves can be generated by a series of excitation cycles over a given time period while capacitance values are changing (such as in between steady-state time points like following exposure of the graphene varactor(s) to a gaseous mixture and before capacitance stops changing in response to analytes within the gaseous mixture). Thus, in accordance with various embodiment herein, the kinetics of capacitance change can be captured (kinetic data) reflecting how capacitance changes during the binding of analytes to the surface of the graphene varactors within an array. This kinetic data (or non-steady-state data) can be used in addition to or instead of the steady-state data to provide enhanced resolution of gaseous samples.

During the non-steady state response phase (or kinetic phase), the measured parameter increases or decreases over time with respect to a baseline value for each measured parameter. The increase or decrease in the measured parameter can be reflected in a plot of change in the measured parameter over time as a positive or negative increase from the baseline value. The kinetics of the change in at least one of the parameters of the graphene varactor response signal can provide a unique kinetic response profile for each unique gaseous mixture. Thus, in some embodiments, the profile of a measured parameter during the non-steady state response phase for each discrete binding detector defines a unique kinetic response profile for each unique gaseous mixture. In contrast, during a steady-state response phase, the measured parameter of the graphene varactor becomes largely consistent over time and the plot of change in measured parameter over time plateaus.

Figure 4:
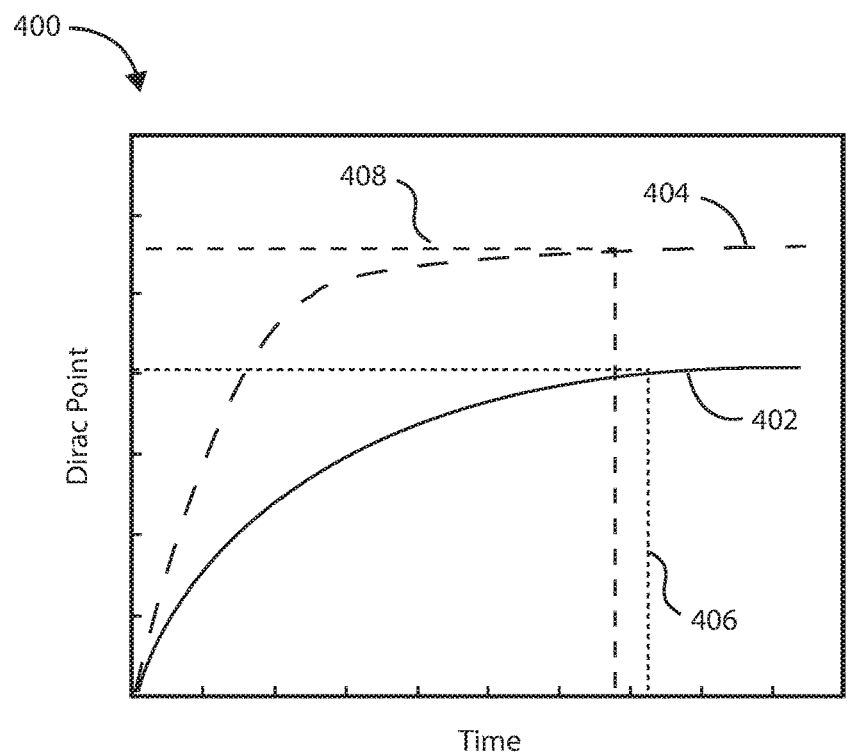
FIG. 4 is a graph showing a change in Dirac point versus time for two graphene varactors in accordance with various embodiments herein.
Figure 5:
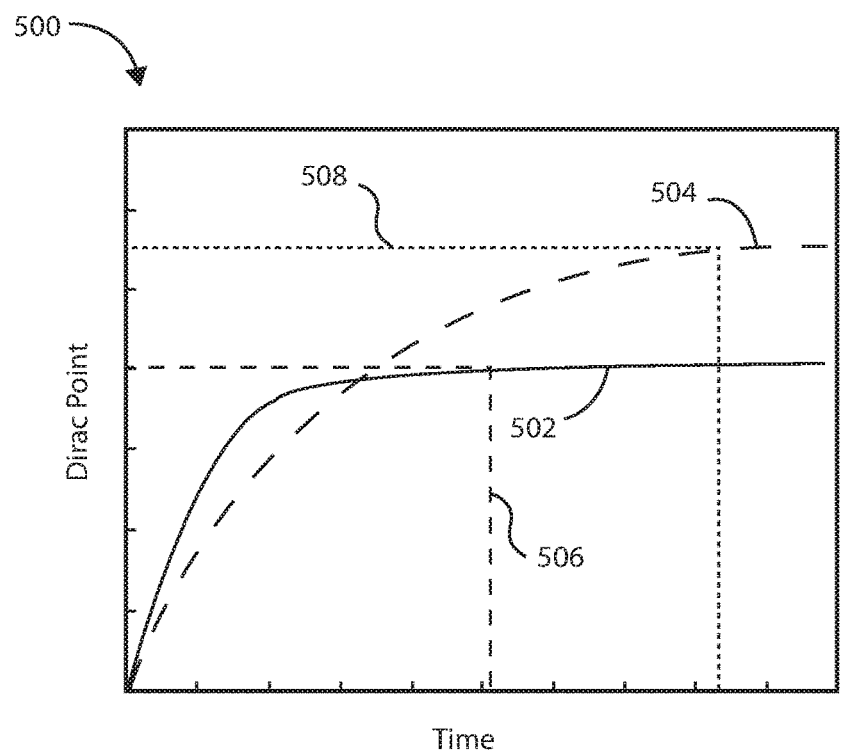
FIG. 5 is a graph showing a change in Dirac point versus time for two graphene varactors in accordance with various embodiments herein.

Referring now to FIGS. 4 and 5, graphs illustrating the kinetics of a change in a graphene varactor parameter versus time for two discrete graphene varactors are shown in accordance with various embodiments herein. While FIGS. 4 and 5 show a change in the Dirac point, it will be appreciated that the change in one or more of the parameters of a graphene varactor response signal can also include a change in the maximum capacitance, a change in the minimum capacitance, a change in the slope of the response signal, or a change in another capacitance related parameter described herein.

The same graphene varactors in the presence of different gaseous mixtures can produce unique response signals that can be used to discriminate one gaseous mixture from another. By way of example, the graph 400 shown in FIG. 4 includes plots of the change in Dirac point versus time for two discrete graphene varactors in the presence of a first gaseous mixture. The change in Dirac point for the first graphene varactor in the presence of a first gaseous mixture is represented as plot 402. The change in Dirac point for the second graphene varactor in the presence of a first gaseous mixture is represented as plot 404. The graph 500 shown in FIG. 5 includes plots of the change in Dirac point versus time for two discrete graphene varactors in the presence of a second gaseous mixture. The change in Dirac point for the first graphene varactor in the presence of a second gaseous mixture is represented as plot 502. The change in Dirac point for the second graphene varactor in the presence of a second gaseous mixture is represented as plot 504.

The first and second gaseous mixtures of FIGS. 4 and 5 can be distinguished from one another based on the unique response signals generated by the graphene varactors in the presence of each of the different gases. For example, the non-steady state phase for plot 402 of FIG. 4 is represented by the portion of the plot that increases from a baseline Dirac point value to a final Dirac point value, as shown within bounded region 406. The non-steady state phase of plot 404 is represented by the portion of the plot that increases from a baseline Dirac point value to a final Dirac point value, as shown within bounded region 408. The plateaus of plot 402 and plot 404 are representative of the steady-state phase for each respective plot.

The non-steady state phase for plot 502 of FIG. 5 is represented by the portion of the plot that increases from a baseline Dirac point value to a final Dirac point value, as shown within bounded region 506. The non-steady state phase of plot 504 is represented by the portion of the plot that increases from a baseline Dirac point value to a final Dirac point value, as shown within bounded region 508. The plateaus of plot 502 and plot 504 are representative of the steady-state phase for each respective plot It will be appreciated that if only considering steady-state values (in this case the starting points and the ending points), the two sets of response signals shown in FIGS. 4 and 5 appear to be the same. However, the non-steady state response (or kinetic response) is much different. Thus, the binding of analytes from the first and second gaseous mixtures to the graphene surfaces define a unique kinetic response profiles for each of the first and second gaseous mixtures that can be used to distinguish the two gaseous mixtures from one another.

Figure 6:
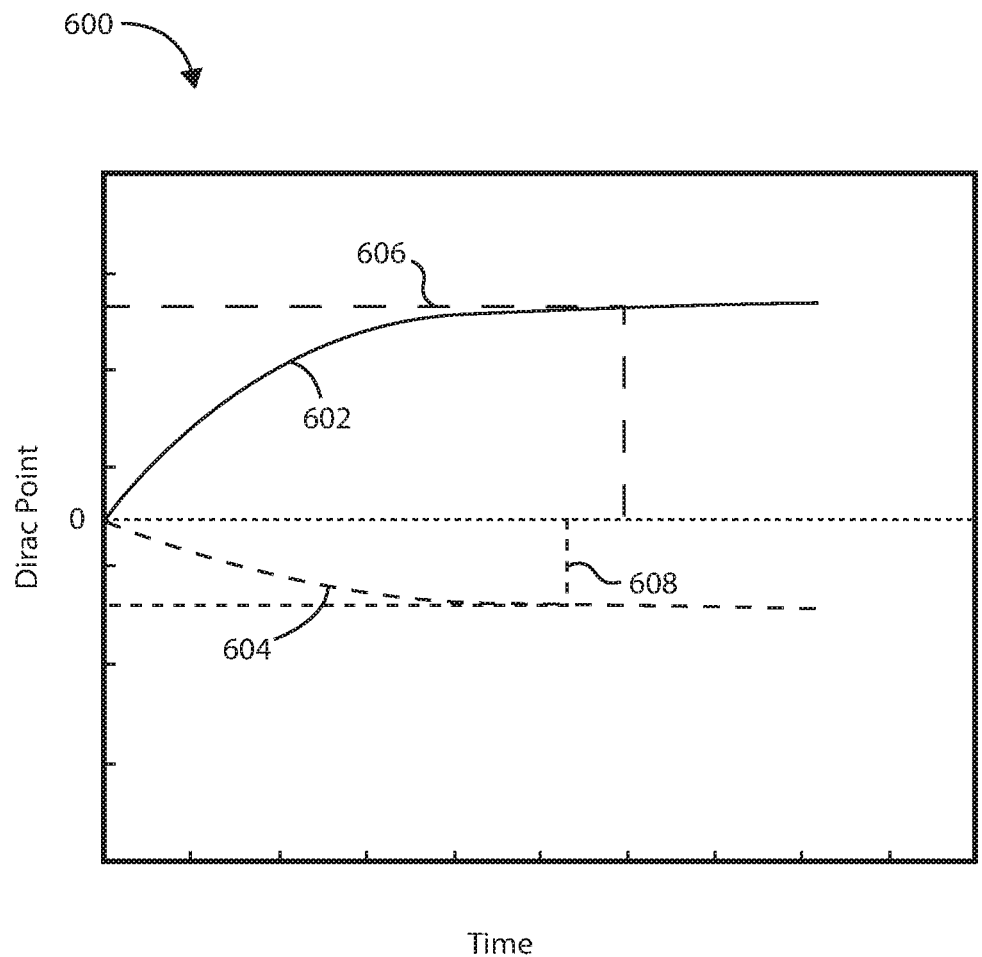
FIG. 6 is a graph showing a change in Dirac point versus time for two graphene varactors in accordance with various embodiments herein.

It will be appreciated that in some embodiments, the response signal in the presence of a gaseous mixture can change in a direction negative to the response signal in the absence of a gaseous mixture (e.g., change of a given capacitance related parameter is not always positive, it can also be negative). Referring now to FIG. 6, a graph 600 showing a change in Dirac point versus time for two graphene varactors is shown in accordance with various embodiments herein. The zero point on the vertical axis simply represents the starting Dirac point and not specifically a Dirac point of 0 V. It will be appreciated that while the parameter plotted in FIG. 6 illustrates a change in the Dirac point, the change can also include a change in the maximum capacitance, a change in the minimum capacitance, of a change in the slope of the response signal, or any of the other capacitance related parameters described herein.

The graph 600 shown in FIG. 6 includes plots of the change in Dirac point versus time for two discrete graphene varactors in the presence of a third gaseous mixture. The change in Dirac point for the first graphene varactor in the presence of a third gaseous mixture is represented as plot 602. The change in Dirac point for the second graphene varactor in the presence of a third gaseous mixture is represented as plot 604. The non-steady state phase for plot 602 of FIG. 6 is represented by the portion of the plot that increases from a baseline Dirac point value to an ending Dirac point value, as shown within bounded region 606. The non-steady state phase of plot 604 is represented by the portion of the plot that increases from a baseline Dirac point value to an ending Dirac point value, as shown within bounded region 608. The plateaus of plot 602 and plot 604 are representative of the steady-state phase for each respective plot. It will be appreciated that the kinetics of the change in Dirac point value versus time for plot 602 and plot 604 define a unique kinetic response profile for the third gaseous mixture.

Figure 7:
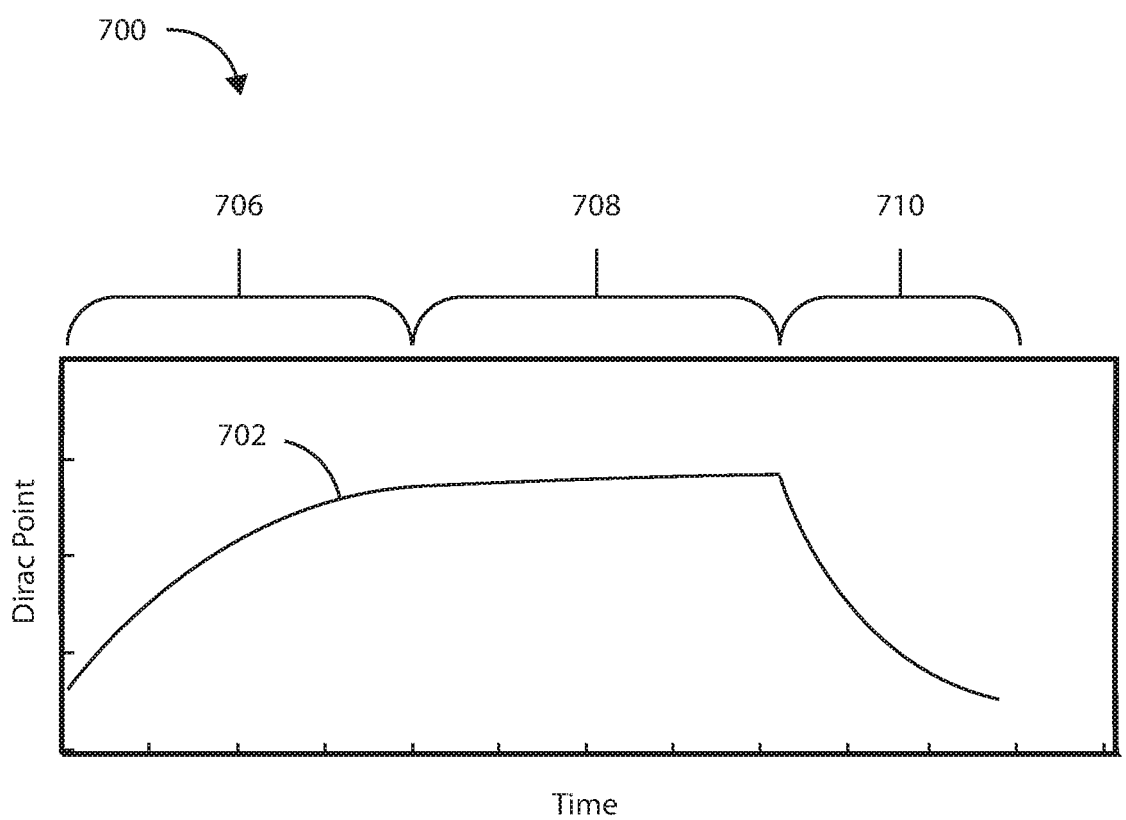
FIG. 7 is graph showing a change in Dirac point versus time for a graphene varactor in accordance with various embodiments herein.

In some embodiments, the graphene sensor response signals can include kinetic phases associated with both the binding (or association) and unbinding (disassociation) of analytes to the receptor surfaces. Referring now to FIG. 7, a graph 700 showing a change in Dirac point versus time for a graphene varactor is shown in accordance with various embodiments herein. The graph 700 shown in FIG. 7 includes a plot of the change in Dirac point versus time for a graphene varactor in the presence of the fourth gaseous mixture. The change in Dirac point for the graphene varactor in the presence of a fourth gaseous mixture is represented as plot 702. The plot of the change in the Dirac point over time includes a non-steady state response phase 706, such as when analyte binding to the surface of the graphene varactor takes place. The plot of the change in the Dirac point over time also includes a steady-state response phase 708, when analyte binding is in a steady state (or equilibrium state). The plot of the change in the Dirac point over time can further include an additional non-steady state response phase 710, such as when analytes unbind from the sensor surface. The additional non-steady state response phase 710 could correspond to various events such as a supply of sample gas being turned off, the chemical sensor being flushed with ambient air or an inert gas, or the like.

Figure 8:
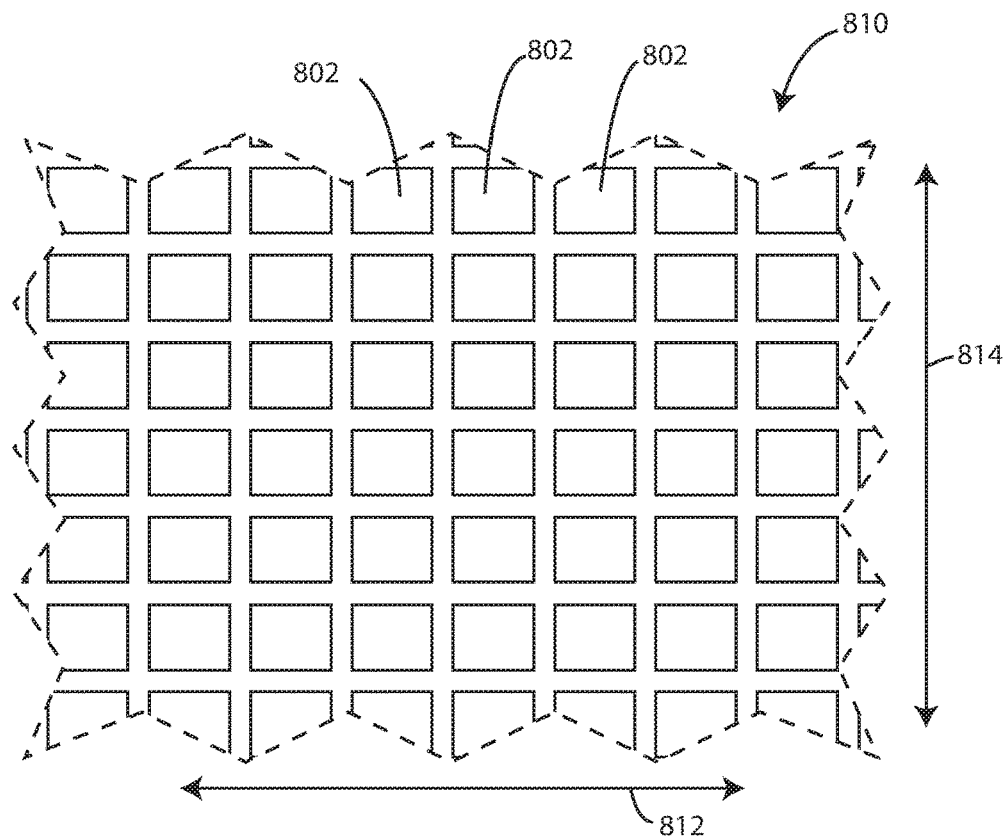
FIG. 8 is a schematic diagram of a portion of a chemical sensor element in accordance with various embodiments herein.

Referring now to FIG. 8, a schematic diagram of a portion of a chemical sensor element 810 is shown in accordance with various embodiments herein. A plurality of graphene varactors 802 can be disposed on the chemical sensor element 810 in an array. In some embodiments, a chemical sensor element can include a plurality of graphene varactors configured in an array. In some embodiments, the plurality of graphene varactors can include identical surface chemistries, while in other embodiments the plurality of graphene varactors can include different surface chemistries from one another. In some embodiments, graphene varactors having the same surface chemistries can be present in duplicate, triplicate, or more, such that data obtained during the excitation cycles can be averaged together to further refine the change observed in the response signals. The graphene varactors herein can be as described in more detail in U.S. Pat. No. 9,513,244, which is herein incorporated by reference in its entirety.

In some embodiments, the graphene varactors can be heterogeneous in that they are different (in groups or as individual graphene varactors) from one another in terms of their binding behavior or specificity with regard a particular analyte. In some embodiments, some graphene varactors can be duplicated, triplicated, or more, for validation purposes but are otherwise heterogeneous from other graphene varactors. Yet in other embodiments, the graphene varactors can be homogeneous. While the graphene varactors 802 of FIG. 8 are shown as boxes organized into a grid, it will be appreciated that the graphene varactors can take on many different shapes (including, but not limited to, various polygons, circles, ovals, irregular shapes, and the like) and, in turn, the groups of graphene varactors can be arranged into many different patterns (including, but not limited to, star patterns, zig-zag patterns, radial patterns, symbolic patterns, and the like).

In some embodiments, the order of specific graphene varactors 802 across the length 812 and width 814 of the measurement zone can be substantially random. In other embodiments, the order can be specific. For example, in some embodiments, a measurement zone can be ordered so that the specific graphene varactors 802 configured to bind to analytes having a lower molecular weight are located farther away from the incoming gas flow relative to specific graphene varactors 802 configured to bind to analytes having a higher molecular weight which are located closer to the incoming gas flow. As such, chromatographic effects which may serve to provide separation between chemical compounds of different molecular weight can be taken advantage of to provide for optimal binding of chemical compounds to corresponding graphene varactors.

The number of graphene varactors can be from about 1 to about 100,000. In some embodiments, the number of graphene varactors can be from about 1 to about 10,000. In some embodiments, the number of graphene varactors can be from about 1 to about 1,000. In some embodiments, the number of graphene varactors can be from about 2 to about 500. In some embodiments, the number of graphene varactors can be from about 10 to about 500. In some embodiments, the number of graphene varactors can be from about 50 to about 500. In some embodiments, the number of graphene varactors can be from about 1 to about 250. In some embodiments, the number of graphene varactors can be from about 1 to about 50.

In some embodiments, each of the graphene varactors suitable for use herein can include at least a portion of one or more electrical circuits. By way of example, in some embodiments, each of the graphene varactors can include all or a portion of one or more passive electrical circuits. In some embodiments, the graphene varactors can be formed such that they are integrated directly on an electronic circuit. In some embodiments, the graphene varactors can be formed such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or non-specific binding, with a component from a biological sample. Many different types of circuits can be used to gather data from chemical sensor elements and will be discussed below in reference to FIGS. 10 and 11.

Figure 9:
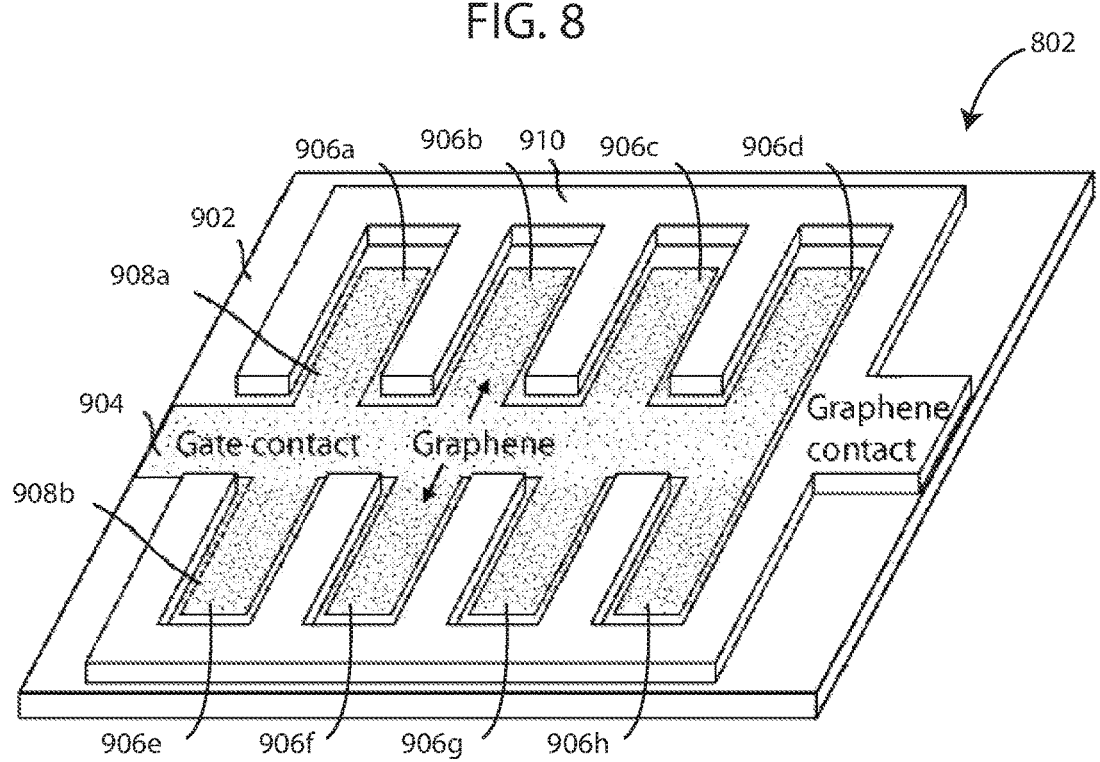
FIG. 9 is a schematic perspective view of a discrete graphene varactor in accordance with various embodiments herein.

In some embodiments, the graphene varactors embodied herein can include graphene-based variable capacitors (or graphene varactors). Referring now to FIG. 9, a schematic view of a graphene varactor 802 is shown in accordance with the embodiments herein. It will be appreciated that graphene varactors can be prepared in various ways with various geometries, and that the graphene varactor shown in FIG. 9 is just one example in accordance with the embodiments herein.

Graphene varactor 802 can include an insulator layer 902, a gate electrode 904 (or "gate contact"), a dielectric layer (not shown in FIG. 9), one or more graphene layers, such as graphene layers 908a and 908b, and a contact electrode 910 (or "graphene contact"). In some embodiments, the graphene layer(s) 908a-b can be contiguous, while in other embodiments the graphene layer(s) 908a-b can be non-contiguous. Gate electrode 904 can be deposited within one or more depressions formed in insulator layer 902. Insulator layer 902 can be formed from an insulative material such as silicon dioxide, formed on a silicon substrate (wafer), and the like. Gate electrode 904 can be formed by an electrically conductive material such as chromium, copper, gold, silver, tungsten, aluminum, titanium, palladium, platinum, iridium, and any combinations or alloys thereof, which can be deposited on top of or embedded within the insulator layer 902. The dielectric layer can be disposed on a surface of the insulator layer 902 and the gate electrode 904. The graphene layer(s) 908a-b can be disposed on the dielectric layer.

Graphene varactor 802 includes eight gate electrode fingers 906a-906h. It will be appreciated that while graphene varactor 802 shows eight gate electrode fingers 906a-906h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Graphene varactor 802 can include one or more contact electrodes 910 disposed on portions of the graphene layers 908a and 908b. Contact electrode 910 can be formed from an electrically conductive material such as chromium, copper, gold, silver, tungsten, aluminum, titanium, palladium, platinum, iridium, and any combinations or alloys thereof. Further aspects of exemplary graphene varactors can be found in U.S. Pat. No. 9,513,244, the content of which is herein incorporated by reference in its entirety.

The capacitance of the graphene varactors can be measured by delivering an excitation current at a particular voltage and/or over a range of voltages. Measuring the capacitance provides data that reflects the binding status of analytes to the graphene varactor(s). Various measurement circuitry can be used to measure the capacitance of the graphene varactor(s), as is discussed in reference to FIGS. 10 and 11. The measurement circuit can include an excitation voltage generator configured to generate a series of excitation cycles over a time period, where each excitation cycle includes delivering a DC bias voltage to the discrete binding detectors at multiple discrete DC bias voltage values across a range of DC bias voltages as discussed in greater detail below.

The measurement circuit can also include a capacitance sensor configured to measure capacitance of the discrete binding detectors resulting from the excitation cycles. The measurement circuit can also include a controller circuit configured to determine the kinetics of change in at least one of a measured capacitance value and a calculated value based on the measured capacitance over the time period.

Figure 10:
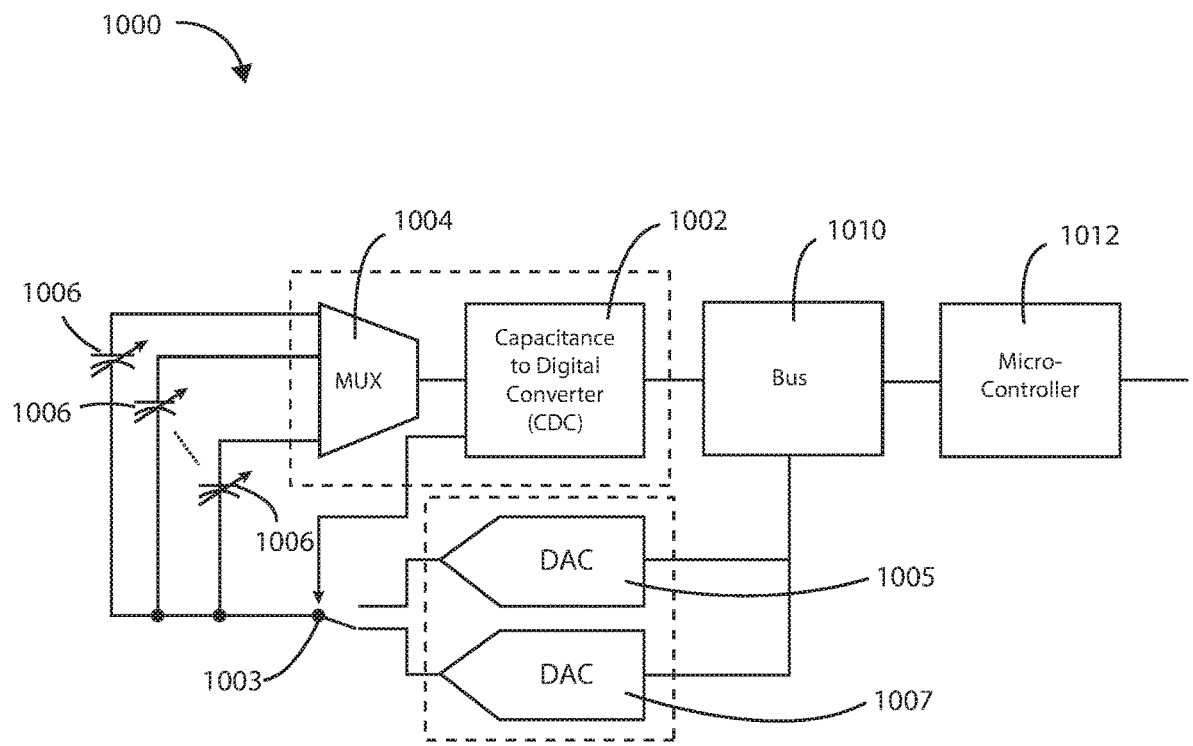
FIG. 10 is a schematic diagram of circuitry to measure the capacitance of a plurality of discrete graphene varactors in accordance with various embodiments herein.

Referring now to FIG. 10, a schematic diagram is shown of measurement circuit 1000 to measure the capacitance of a plurality of graphene sensors in accordance with various embodiments herein. The measurement circuit 1000 can include a capacitance to digital converter (CDC) 1002 in electrical communication with a multiplexor 1004. The multiplexor 1004 can provide selective electrical communication with a plurality of graphene varactors 1006. The connection to the other side of the graphene varactors 1006 can be controlled by a switch 1003 (as controlled by the CDC) and can provide selective electrical communication with a first digital to analog converter (DAC) 1005 and a second digital to analog converter (DAC) 1007. The other side of the DACs 1005, 1007 can be connected to a bus device 1010, or in some cases, the CDC 1002. The circuitry can further include a microcontroller 1012, which will be discussed in more detail below.

In this case, the excitation signal from the CDC controls the switch between the output voltages of the two programmable Digital to Analog Converters (DACs). The programmed voltage difference between the DACs determines the excitation amplitude, providing an additional programmable scale factor to the measurement and allowing measurement of a wider range of capacitances than specified by the CDC. The bias voltage at which the capacitance is measured is equal to the difference between the bias voltage at the CDC input (via the multiplexor, usually equal to VCC/2, where VCC is the supply voltage) and the average voltage of the excitation signal, which is programmable. In some embodiments, buffer amplifiers and/or bypass capacitance can be used at the DAC outputs to maintain stable voltages during switching.

The above calculated aspects can be used for various diagnostic purposes. In some cases, the above calculated aspects can be indicative of the identity and/or concentrations of specific volatile organic components of a gas sample. As such, each of the calculated values above can serve as a distinct piece of data that forms part of a pattern for a given subject and/or given gas sample. As also described elsewhere herein, the pattern can then be matched against preexisting patterns, or patterns identified in real-time, derived from large stored data sets through techniques such as machine learning or other techniques, wherein such patterns are determined to be characteristic of various conditions or disease states. The above calculated aspects can also be put to other purposes, diagnostic and otherwise.

In some embodiments, calculations such as those described above can be performed by a controller circuit. The controller circuit can be configured to receive an electrical signal reflecting the capacitance of the graphene varactors. In some embodiments, the controller circuit can include a microcontroller to perform these calculations. In some embodiments, the controller circuit can include a microprocessor in electrical communication with the measurement circuit. The microprocessor system can include components such as an address bus, a data bus, a control bus, a clock, a CPU, a processing device, an address decoder, RAM, ROM and the like. In some embodiments, the controller circuit can include a calculation circuit (such as an application specific integrated circuit—ASIC) in electrical communication with the measurement circuit.

The controller circuit can be configured to calculate a rate of change of a measured capacitance or a calculated value based on measured capacitance over the time period at multiple discrete DC bias voltages. In some embodiments, the controller circuit can be configured to calculate an average rate of change of measured capacitance over the time period at multiple discrete DC bias voltages. In other embodiments, the controller circuit can be configured to determine the start of a steady-state response phase from each of the discrete binding detectors by assessing a rate of change of measured capacitance over the time period.

In some embodiments the controller circuit can be configured to determine the start of a non-steady state response phase from each of the discrete binding detectors by assessing a rate of change of measured capacitance over the time period. In some embodiments, when the rate of change exceeds a threshold value, the start of a non-steady state response phase can be recognized. In some embodiments, the controller circuit can be configured to determine the end of the non-steady state response phase from each of the discrete binding detectors by assessing a rate of change of measured capacitance over the time period. In some embodiments, the end of a non-steady state response phase (and the beginning of a steady state response phase) can be recognized based on the rate of change exceeding a threshold value. The controller circuit can be configured to calculate the rate of change in the Dirac point for the discrete binding detectors over the time period. The controller circuit can be configured to determine a maximum rate of change for capacitance for the discrete binding detectors over the time period. The profile of measured capacitance during the non-steady state response phase for each discrete binding detector defines a unique kinetic response profile for a unique gaseous mixture.

In addition, in some embodiments, the system can include a nonvolatile memory. In some embodiments, the nonvolatile memory can be configured to store measured capacitance values for the discrete binding detectors across a range of DC bias voltages. In other embodiments, the nonvolatile memory can be configured to store a baseline capacitance for the discrete binding detectors across a range of DC bias voltages. In some embodiments, the nonvolatile memory can be where sensitivity calibration information for the graphene varactors is stored.

By way of example, the graphene varactors could be tested in a production facility, where sensitivity to various analytes such as VOC's can be determined and then stored on an EPROM or similar component. In addition, or alternatively, sensitivity calibration information can be stored in a central database and referenced with a chemical sensor element serial number when subject data is sent to a central location for analysis and diagnosis. These components can be included with any of the pieces of hardware described herein.

In some embodiments herein, components can be configured to communicate over a network, such as the internet or a similar network. In various embodiments, a central storage and data processing facility can be included. In some embodiments, data gathered from sensors in the presence of the subject (local) can be sent to the central processing facility (remote) via the internet or a similar network, and the pattern from the particular subject being evaluated can be compared to those of thousands or millions of other subjects, many of whom have been previously diagnosed with various conditions and wherein such condition data has been stored. Pattern matching algorithms can be used to find other subjects or classes of subjects (for example disease or condition specific classes) to which the current subject's pattern is most similar. Each class of subjects can include a predetermined likelihood of having a given condition or disease state. In this manner, after pattern matching a likelihood of having a given condition or disease state can be provided back across the data network to the facility where the subject is currently located.

In some embodiments, measurement circuits suitable for use herein can include active and passive sensing circuits. Such circuitry can implement wired (direct electrical contact) or wireless sensing techniques. Referring now to FIG.

Figure 11:
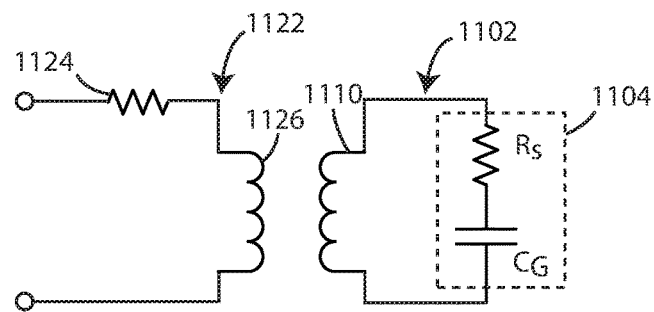
FIG. 11 is a schematic diagram of a passive sensor circuit and a portion of a reading circuit is shown in accordance with various embodiments herein.

11, a schematic diagram of a passive sensor circuit 1102 and a portion of a reading circuit 1122 is shown in accordance with various aspects herein. In some embodiments, the passive sensor circuit 1102 can include a metal-oxide-graphene varactor 1104 (wherein RS represents the series resistance and CG represents the varactor capacitor) coupled to an inductor 1110. In some embodiments, the reading circuit 1122 can include a reading coil having a resistance 1124 and an inductance 1126. However, it will be appreciated that the circuits shown in FIGS. 10 and 11 are merely exemplary approaches. Many different approaches are contemplated herein.

Bias Voltages/Excitation Cycles

Response signals herein can be gathered by measuring capacitance over a range of DC bias voltages. In order to determine a particular capacitance parameter, such as the Dirac point, a current is applied to the graphene varactor at a plurality of bias voltages (an example of an excitation cycle). This can result in data such as that shown in one of the curves in FIGS. 2 and 3. If only a single measurement of the Dirac point (or another capacitive parameter) were desired, this could be accomplished with a single excitation cycle. However, in order to track the kinetics of how a capacitance parameter changes, a series of excitation cycles can be applied, with each representing applying a bias voltage at a plurality of different voltages. Thus, data representing the equivalent of the curves shown in FIGS. 2 and 3 (e.g., data representing the relationship between bias voltage and capacitance) can be generated at a plurality of time points (such as successive time points) in order to determine the kinetics of how the Dirac point (or another capacitive parameter) changes during a non-steady state phase.

Many different ranges of DC bias voltages can be used for each excitation cycle. In some embodiments, the DC bias voltages used in the methods herein can include from –3 V, –2.5 V, –2.0 V, –1.5 V, –1.0 V, –0.5 V, 0.5 V, 1.0 V, 1.5 V, 2.0 V, 2.5 V, 3.0 V. It will be appreciated that the DC bias voltages used in the methods herein can include delivering a DC bias voltage within a range, wherein any of the forgoing voltages can serve as the lower or upper bound of the range, provided that the lower bound of the range is a value less than the upper bound of the range.

In various embodiments, a "sweep" across a voltage range can include a number discrete measurements being made during the sweep at a number of discrete bias voltages across the voltage range. In some embodiments, an excitation cycle herein can include a forward sweep (from low bias voltages to high bias voltages). In some embodiments, an excitation cycle herein can include a backward sweep (from high bias voltages to low bias voltages). In some embodiments, an excitation cycle herein can include both a forward and backward sweep, or any combination thereof. In some embodiments, a bias voltage of 0 V or 0.5 V (or other "reset" voltage) can be applied at the end of an excitation cycle and before the next excitation cycle or at the end of all testing.

The length of time for each excitation cycle can depend on various factors including the total number of measurements made of capacitance during the cycle, the total bias voltage range being covered, the voltage step size for each measurement, the time for each measurement, etc. In some embodiments, the time period for each excitation cycle can be about 0.1, 0.5, 1, 2, 3, 4, 5, 6, 7, 8, 9, 10, 12, 15, 20, 30, 45, 60, 120 seconds or more. It will be appreciated that the time period for each excitation cycle can include a range, wherein any of the forgoing time points can serve as the lower or upper bound of the range, provided that the lower bound of the range is a value less than the upper bound of the range.

In some embodiments, the total time for all excitation cycles can be configured to match the total amount of time for testing of a gaseous sample. In some embodiments, the total time for all excitation cycles can be configured to be equal to a predetermined time that covers a period of interest. In some embodiments, the total time for all excitation cycles can be configured to be equal or greater than the total amount of time for a non-steady state phase (or kinetic phase). In some embodiments, the controller circuit can be configured to determine the start of a non-steady state response phase from each of the discrete binding detectors by assessing a rate of change of measured capacitance over time and initiate excitation cycles at that point. In some embodiments, the controller circuit can be configured to initiate excitation cycles when a signal is received indicating the start of a particular test of gaseous sample, such as receiving a sign from a flow sensor that a sample gas is starting to flow to the discrete binding detectors. In some embodiments, the controller circuit can be configured to determine the end of a non-steady state phase by assessing a rate of change of measured capacitance over time and terminating excitation cycles at that point or reducing the frequency of excitation cycles at that point.

In various embodiments, the total time period for generating a series of excitation cycles (the total time for all excitation cycles) can include from 10 seconds to 1200 seconds. In some embodiments, the time period for generating a series of excitation cycles can include from 30 seconds to 180 seconds. In some embodiments, the time period for generating a series of excitation cycles can include from 10, 15, 20, 25, 30, 40, 45, 60, 90, 120, 150, 180, 360, 540, 720, 1080, 1200 seconds or more. It will be appreciated that the time period for generating a series of excitation cycles can include a range, wherein any of the forgoing time points can serve as the lower or upper bound of the range, provided that the lower bound of the range is a value less than the upper bound of the range.

In some embodiments, stepping through the range of DC bias voltages can include stepping through the range of DC bias voltages in predetermined increments, such as 50 mV increments. In some embodiments, stepping through the range of DC bias voltages can include stepping through the range of DC bias voltages in 10 mV increments. Stepping through the range of DC bias voltages can be performed at voltage increments of 1 mV, 5 mV, 10 mV, 25 mV, 50 mV, 75 mV, 100 mV, 125 mV, 150 mV, 200 mV, 300 mV, 400 mV, or 500 mV, or by a stepped amount falling within a range between any of the foregoing.

Capacitance Parameters

Many different capacitance related parameters can be calculated based on the capacitance data. For example, parameters that can be calculated include maximum slope of capacitance to voltage, change in maximum slope of capacitance to voltage over a baseline value, minimum slope of capacitance to voltage, change in minimum slope of capacitance to voltage over a baseline value, minimum capacitance, change in minimum capacitance over a baseline value, voltage at minimum capacitance (Dirac point), change in voltage at minimum capacitance, maximum capacitance, change in maximum capacitance, ratio of maximum capacitance to minimum capacitance, response time constants, and ratios of any of the foregoing between different graphene sensors and particularly between different graphene sensors having specificity for different analytes.

Kinetics Analysis

Many different parameters can be calculated using the controller circuit or another device and the non-steady state phase (or kinetic phase) data. For example, in some embodiments, parameters calculated can include maximum rate of change during the kinetic phase, time to reach a relative degree of change (such as time to hit a magnitude of 80% of the total change), the function providing the best fit curve (e.g., first, second, third or fourth degree polynomial; exponential functions, sums of exponential functions, etc.), coefficients of a best fit curve, characteristic time constant(s), total time of the kinetic phase, and the like. However, it will be appreciated that in some embodiments none of these values need to be explicitly calculated and the kinetic phase data (with or without corresponding steady-state phase date) can be used in machine learning analysis such as that described herein.

By way of example, as a chemical sensor is exposed to new concentrations of analyte(s), the equilibrium of analyte binding to the surface of the chemical sensor will adjust according to the concentration of analyte above the sensor(s). The binding kinetics of an analyte or mixture of analytes can be analyzed using real-time data based on the rate of association of analyte and the rate of dissociation of analyte. The rate of association of analyte (i.e., analyte binding) can be represented by equation [1] and the rate of disassociation of analyte (i.e., analyte unbinding) can be represented by equation [2]:

$$\frac{dC_{AS}}{dt} = k_{on} \cdot C_A \cdot C_S \quad [1]$$

$$\frac{dC_{AS}}{dt} = -k_{off} \cdot C_{AS} \quad [2]$$

where $k_{on}$ is the association rate of analyte binding to the sensor in $(mol/L)^{-1} s^{-1}$, $k_{off}$ is the dissociation rate of analyte from the sensor in $s^{-1}$, $C_A$ is the concentration of analyte, $C_S$ is the concentration of binding sites on the sensor, and $C_{AS}$ is the concentration of analyte bound to the sensor.

The binding of analyte to the sensor at any given time, t, and any given concentration, c, can be represented by an integration of the rate equations [1] and [2], as shown in equation [3]:

$$f(t, c) = f_{eq}(c) \cdot [1 - \exp\{-k_{on}^{obs} \cdot t\}] \quad [3]$$

where $k_{on}^{obs}$ is the observable association rate and $f_{eq}$ is a terminal value that the chemical sensor signal approaches during analyte binding with the sensor. The observable association rate $k_{on}^{obs}$ can be defined by equation [4]:

$$k_{on}^{obs} = c \cdot k_{on} + k_{off} \quad [4]$$

The terminal value $f_{eq}$ depends on analyte concentration and is governed by a characteristic time constant $\tau_{on}^{obs}$, where the characteristic time constant is represented by equation [5]:

$$\tau_{on}^{obs} = 1/k_{on}^{obs} \quad [5]$$

Thus, as analyte concentration changes, so does the chemical sensor signal.

The rate of dissociation of analyte from the chemical sensor can be observed by removing the analyte(s) from the environment of the chemical sensor. This can be accomplished by flushing the chemical sensor with ambient air, an inert gas, and the like. The dissociation of analyte from the sensor can be represented by equation [6]:

$$f(t) = \alpha \cdot \exp\{-k_{off} \cdot t\} \quad [6]$$

where $k_{off}$ is the dissociation rate constant of analyte unbinding from the sensor in $s^{-1}$ and $\alpha$, or amplitude, represents the fraction of analyte bound to the chemical sensor just before removal of analyte from the chemical sensor. Dissociation of analyte from the chemical sensor is governed by the dissociation rate constant, $k_{off}$, and the dissociation time constant $\tau_{off}$ in sec (s); the dissociation time constant is represented by equation [7]:

$$\tau_{off} = 1/k_{off} \quad [7]$$

Classification and Pattern Matching

Classifying the data sets obtained (including one or both of kinetic phase data and steady-state phase data) into one or more preestablished classifications (such as disease state or health condition classifications) can be performed according to many different machine learning techniques, such as pattern recognition. Classification can include comparing the sample data set against one or more previously determined patterns using a pattern matching or pattern recognition algorithm to determine the pattern that is the best match, wherein the specific previously determined pattern that is the best match indicates the disease state of the subject.

By way of example, patterns amongst large sets of subject data may be originally identified through machine learning analysis or another similar algorithmic technique. Patterns associated with specific disease state classifications can be derived from labeled "training" data (supervised learning) or in the absence of labeled data (unsupervised learning).

Algorithms for pattern matching used herein can include, but are not limited to, classification algorithms (supervised algorithms predicting categorical labels), clustering algorithms (unsupervised algorithms predicting categorical labels), ensemble learning algorithms (supervised meta-algorithms for combining multiple learning algorithms together), general algorithms for predicting arbitrarily-structured sets of labels, multilinear subspace learning algorithms (predicting labels of multidimensional data using tensor representations), real-valued sequence labeling algorithms (predicting sequences of real-valued labels), regression algorithms (predicting real-valued labels), and sequence labeling algorithms (predicting sequences of categorical labels).

Classification algorithms can include parametric algorithms (such as linear discriminant analysis, quadratic discriminant analysis, and maximum entropy classifier) and nonparametric algorithms (such as decision trees, kernel estimation, naïve Bayes classifier, neural networks, perceptrons, and support vector machines). Clustering algorithms can include categorical mixture models, deep learning methods, hierarchical clustering, K-means clustering, correlation clustering, and kernel principal component analysis. Ensemble learning algorithms can include boosting, bootstrap aggregating, ensemble averaging, and mixture of experts. General algorithms for predicting arbitrarily-structured sets of labels can include Bayesian networks and Markov random fields. Multilinear subspace learning algorithms can include multilinear principal component analysis (MPCA). Real-valued sequence labeling algorithms can include Kalman filters and particle filters. Regression algorithms can include both supervised (such as Gaussian process regression, linear regression, neural networks and deep learning methods) and unsupervised (such as independent component analysis and principal components analysis) approaches. Sequence labeling algorithms can include both supervised (such as conditional random fields, hidden Markov models, maximum entropy Markov models, and recurrent neural networks) and unsupervised (hidden Markov models and dynamic time warping) approaches.

Methods

Figure 12:
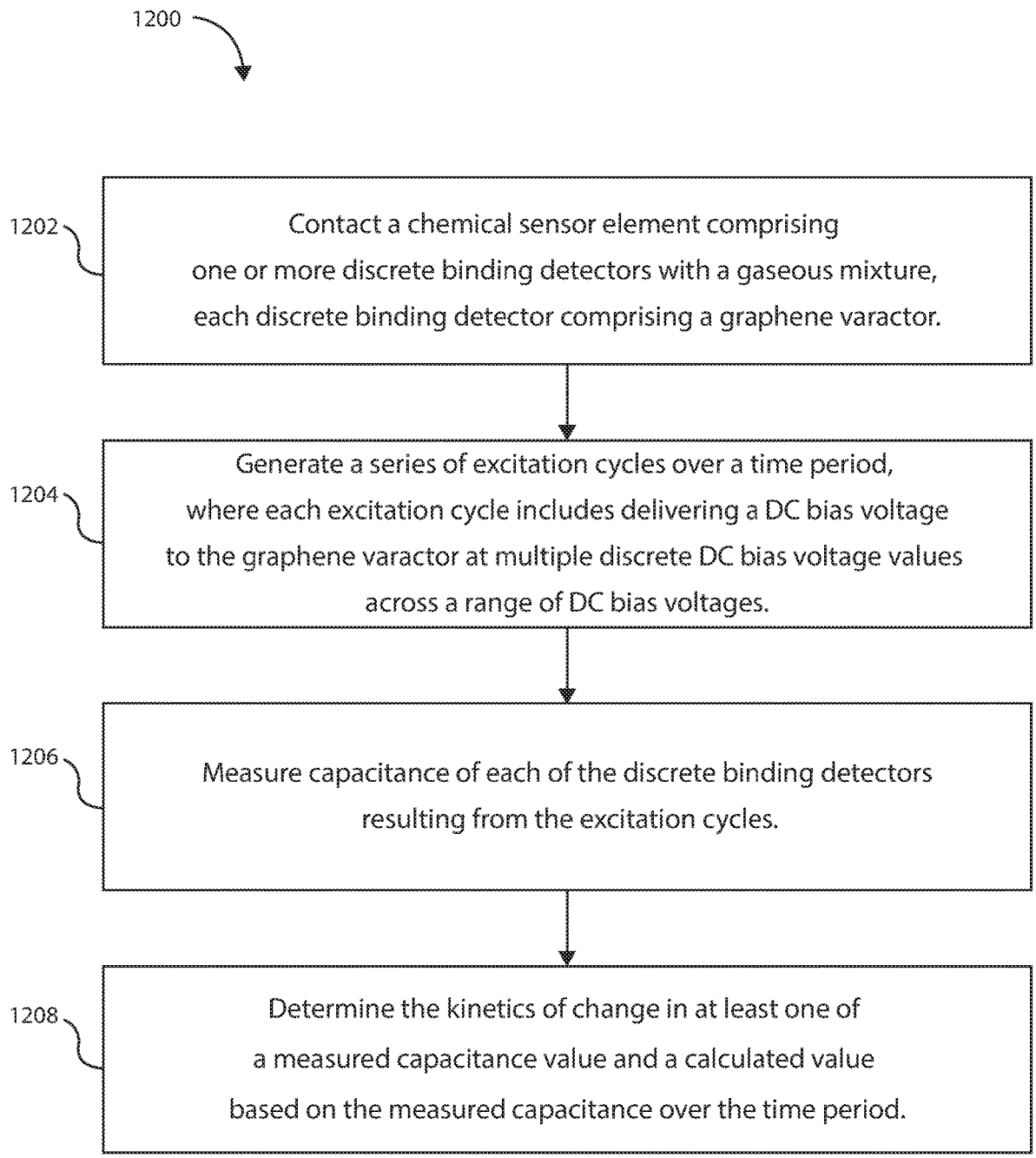
FIG. 12 is a schematic flow diagram of a method for measuring analyte presence on a chemical sensor element in accordance with various embodiments herein.

Embodiments herein can include methods for measuring analyte presence on a chemical sensor element using a kinetic response system. Referring now to FIG. 12, a method 1200 for measuring analyte presence on a chemical sensor element using a kinetic response system is shown in accordance with various embodiments herein. The method 1200 can include contacting a chemical sensor element including one or more discrete binding detectors with a gaseous mixture, each discrete binding detector including a graphene varactor at 1202. The method 1200 can include generating a series of excitation cycles over a time period, where each excitation cycle includes delivering a DC bias voltage to the graphene varactor at multiple discrete DC bias voltage values across a range of DC bias voltages at 1204. The method 1200 can include measuring capacitance of each of the discrete binding detectors resulting from the excitation cycles at 1206. The method 1200 can include determining the kinetics of change in at least one of a measured capacitance value and a calculated value based on the measured capacitance over the time period at 1208.

In various embodiments, calculating the rate of change of a measured parameter can be included in the methods herein. In some embodiments, the method can include calculating a rate of change of a measured capacitance or a calculated value based on measured capacitance over the time period. In some embodiments, the method can include calculating an average rate of change of measured capacitance over the time period at multiple discrete DC bias voltages. In some embodiments the measured capacitance can include a maximum capacitance or a minimum capacitance. In some embodiments, the method can include calculating the rate of change in the Dirac point for the discrete binding detectors over the time period. In some embodiments, the method can include calculating a rate of change of a shift in the Dirac point or a calculated value based on a shift in the Dirac point over the time period. In other embodiments, the method can include calculating a rate of change in the slope of the response signal or a calculated value based on a change in the response signal over the time period.

The methods herein can include determining a non-steady state response phase and/or a steady-state response phase for the graphene varactor response signal. In some embodiments, the method can include determining the start of a steady-state response phase from each of the discrete binding detectors by assessing a rate of change of measured capacitance over the time period. In some embodiments, the method can include determining the start of a non-steady state response phase from each of the discrete binding detectors by assessing a rate of change of measured capacitance over the time period. In other embodiments, the method can include determining the end of the non-steady state response phase from each of the discrete binding detectors by assessing a rate of change of a measured parameter over the time period, where the start of the non-steady state response phase and the end of the non-steady state response phase for the discrete binding detectors defines a unique non-steady state response profile for a unique gaseous mixture.

In some embodiments, determining the start of the non-steady state response phase comprises determining the start of a kinetic response phase. In some embodiments, the method can include determining the start or end of the kinetic response phase from each of the discrete binding detectors by assessing a rate of change of measured parameter over the time period, and where the start of the kinetic response phase and the end of the kinetic response phase for the discrete binding detectors defines a unique kinetic response profile for a unique gaseous mixture.

The method can also include distinguishing one unique gaseous mixture from another unique gaseous mixture based on the unique kinetic response profile of the unique gaseous mixtures. The methods herein can include contacting the chemical sensor element with an inert gas and detecting unbinding of analytes from each of the discrete binding detectors. The methods herein can include contacting the chemical sensor element with a gas other than a sample gas (such as an inert gas or ambient air) and detecting a full return of each of the discrete binding detectors back toward a baseline capacitance value (appreciating that even in the absence of the sample gas the capacitance may not return all the way back to the original baseline value). In some embodiments, returning the response signal to a baseline capacitance value can include heating the chemical sensor element while under a vacuum to fully return the response signal to a baseline value.

In some embodiments, the methods herein can include contacting and/or storing the chemical sensor element with an inert gas prior to use to maintain a baseline capacitance value before contacting the chemical sensor element with a gaseous mixture. In other embodiments, the methods herein can include contacting the chemical sensor element with an inert gas in combination with a gaseous mixture. In some embodiments, the methods can include contacting the sensor with ambient air or filtered ambient air.

In some embodiments, a graphene varactor can be exposed to ambient air, filtered ambient air, or an inert gas and a response signal can be measured. The graphene varactor can then be exposed to a gaseous mixture, such as an exhaled breath mixture, and a response signal can be measured. The graphene varactor can then be exposed again to ambient air, filtered ambient air, or an inert gas and a response signal can be measured a final time.

Delivering a DC bias voltage to the graphene varactor at multiple discrete DC bias voltage values across a range of DC bias voltages can include stepping through the range of DC bias voltages. Methods herein can also utilize memory for storing measured capacitance values for each of the discrete binding detectors across the range of DC bias voltages delivered to each detector. The methods can include storing at least 100 measured capacitance values are into memory for each discrete binding detector across the range of DC bias voltages.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A kinetic response system for measuring analyte presence on a chemical sensor element comprising:
 a chemical sensor element comprising one or more discrete binding detectors, each discrete binding detector comprising a graphene varactor;
 a measurement circuit comprising an excitation voltage generator configured to generate a series of excitation cycles over a time period, wherein each excitation cycle includes delivering a DC bias voltage to the discrete binding detectors at multiple discrete DC bias voltage values across a range of DC bias voltages; and
 a capacitance sensor configured to measure capacitance of the discrete binding detectors resulting from the excitation cycles; and
 a controller circuit configured to determine a kinetic change in at least one of a measured capacitance value and a calculated value based on the measured capacitance over the time period.

2. The kinetic response system of claim 1, wherein the controller circuit is configured to calculate a rate of change of a measured capacitance or a calculated value based on measured capacitance over the time period at multiple discrete DC bias voltages.

3. The kinetic response system of claim 1, wherein the controller circuit is configured to calculate an average rate of change of measured capacitance over the time period at multiple discrete DC bias voltages.

4. The kinetic response system of claim 1, wherein the controller circuit is configured to determine the start of a steady-state response phase from each of the discrete binding detectors by assessing a rate of change of measured capacitance over the time period.

5. The kinetic response system of claim 1, wherein the controller circuit is configured to determine the start of a non-steady state response phase from each of the discrete binding detectors by assessing a rate of change of measured capacitance over the time period.

6. The kinetic response system of claim 5, wherein the controller circuit is configured to determine the end of the non-steady state response phase from each of the discrete binding detectors by assessing a rate of change of measured capacitance over the time period; and wherein the profile of measured capacitance during the non-steady state response phase for each discrete binding detector defines a unique kinetic response profile for a unique gaseous mixture.

7. The kinetic response system of claim 1, wherein the controller circuit is configured to calculate the rate of change in the Dirac point for the discrete binding detectors over the time period.

8. The kinetic response system of claim 1, wherein the controller circuit is configured to determine a maximum rate of change for capacitance for the discrete binding detectors over the time period.

9. The kinetic response system of claim 1, further comprising a flow control valve in fluid communication with an upstream flow path relative the chemical sensor element.

10. A method for measuring analyte presence on a chemical sensor element using a kinetic response system comprising:
 contacting a chemical sensor element comprising one or more discrete binding detectors with a gaseous mixture, each discrete binding detector comprising a graphene varactor;
 generating a series of excitation cycles over a time period, wherein each excitation cycle includes delivering a DC bias voltage to the graphene varactor at multiple discrete DC bias voltage values across a range of DC bias voltages; and
 measuring capacitance of each of the discrete binding detectors resulting from the excitation cycles; and
 determining a kinetic change in at least one of a measured capacitance value and a calculated value based on the measured capacitance over the time period.

11. The method of claim 10, further comprising calculating a rate of change of a measured capacitance or a calculated value based on measured capacitance over the time period.

12. The method of claim 10, further comprising calculating an average rate of change of measured capacitance over the time period at multiple discrete DC bias voltages.

13. The method of claim 10, further comprising determining the start of a steady-state response phase from each of the discrete binding detectors by assessing a rate of change of measured capacitance over the time period.

14. The method of claim 10, further comprising determining the start of a non-steady state response phase from each of the discrete binding detectors by assessing a rate of change of measured capacitance over the time period.

15. The method of claim 14, further comprising determining the end of the non-steady state response phase from each of the discrete binding detectors by assessing a rate of change of measured capacitance over the time period; and
 wherein the start of the non-steady state response phase and the end of the non-steady state response phase for the discrete binding detectors defines a unique kinetic response profile for a unique gaseous mixture.

16. The method of claim 15, further comprising distinguishing one unique gaseous mixture from another unique gaseous mixture based on the unique kinetic response profile of the unique gaseous mixtures.

17. The method of claim 10, further comprising calculating the rate of change in the Dirac point for the discrete binding detectors over the time period.

18. The method of claim 10, further comprising contacting the chemical sensor element with a gas other than a sample gas and detecting a return of each of the discrete binding detectors back toward a baseline capacitance valve.

19. The method of claim 10, wherein the range of range of DC bias voltages comprises from −3 V to 3 V.

20. The method of claim 10, wherein delivering a DC bias voltage to the graphene varactor at multiple discrete DC bias voltage values across a range of DC bias voltages comprises stepping through the range of DC bias voltages in 50 mV increments.

* * * * *